United States Patent
Bothof et al.

(10) Patent No.: US 8,652,582 B2
(45) Date of Patent: Feb. 18, 2014

(54) METHOD OF MAKING LIGAND FUNCTIONALIZED SUBSTRATES

(75) Inventors: Catherine A. Bothof, Stillwater, MN (US); Yi He, Roseville, MN (US); Jerald K. Rasmussen, Woodville, MN (US); Kannan Seshadri, Woodbury, MN (US); Clinton P. Waller, Jr., White Bear Lake, MN (US); Douglas E. Weiss, Golden Valley, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 552 days.

(21) Appl. No.: 12/937,458

(22) PCT Filed: May 26, 2009

(86) PCT No.: PCT/US2009/045110
§ 371 (c)(1),
(2), (4) Date: Oct. 12, 2010

(87) PCT Pub. No.: WO2009/148869
PCT Pub. Date: Dec. 10, 2009

(65) Prior Publication Data
US 2011/0033633 A1 Feb. 10, 2011

Related U.S. Application Data

(60) Provisional application No. 61/057,517, filed on May 30, 2008.

(51) Int. Cl.
*C08F 2/46* (2006.01)
(52) U.S. Cl.
USPC .............................. 427/493; 427/496; 427/508
(58) Field of Classification Search
USPC .......................................... 427/496, 493, 508
See application file for complete search history.

(56) References Cited

U.S. PATENT DOCUMENTS

| | | | |
|---|---|---|---|
| 1,529,256 A | 3/1925 | Kelley |
| 2,945,006 A | 7/1960 | Minsk |
| 3,352,424 A | 11/1967 | Guebert |
| 3,849,241 A | 11/1974 | Butin et al. |
| 3,876,738 A | 4/1975 | Marinaccio et al. |
| 3,928,517 A | 12/1975 | Knight et al. |

(Continued)

FOREIGN PATENT DOCUMENTS

| CA | 2422738 | 4/2002 |
|---|---|---|
| EP | 0 632 329 | 1/1995 |

(Continued)

OTHER PUBLICATIONS

Kolarz, et al., "New selective resin with guanidyl groups," Reactive & Functional Polymers, vol. 36, pp. 185-195, 1998.

(Continued)

*Primary Examiner* — Robert S Walters, Jr.
(74) *Attorney, Agent, or Firm* — Kent S. Kokko

(57) ABSTRACT

Ligand functionalized substrates, methods of making ligand functionalized substrates, and methods of using functionalized substrates are disclosed. The ligand functionalized substrate may be described as the grafted reaction product of a substrate and a ligand monomer of Formula I:

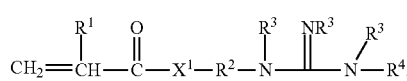

16 Claims, 1 Drawing Sheet

(56) References Cited

U.S. PATENT DOCUMENTS

| | | |
|---|---|---|
| 4,118,531 A | 10/1978 | Hauser |
| 4,157,418 A | 6/1979 | Heilmann |
| 4,266,044 A | 5/1981 | Timmerman |
| 4,339,473 A | 7/1982 | D'Agostino et al. |
| 4,340,057 A | 7/1982 | Bloch et al. |
| 4,346,142 A | 8/1982 | Lazear |
| T103,601 I4 | 11/1983 | Repetti |
| 4,473,474 A | 9/1984 | Ostreicher et al. |
| 4,529,256 A | 7/1985 | Kretzschmar et al. |
| 4,539,256 A | 9/1985 | Shipman |
| 4,563,388 A | 1/1986 | Bonk et al. |
| 4,618,533 A | 10/1986 | Steuck |
| 4,707,265 A | 11/1987 | Barnes, Jr. et al. |
| 4,726,989 A | 2/1988 | Mrozinski |
| 4,734,208 A | 3/1988 | Pall et al. |
| 4,773,903 A | 9/1988 | Weisman et al. |
| 4,837,067 A | 6/1989 | Carey, Jr. et al. |
| 4,867,881 A | 9/1989 | Kinzer |
| 4,885,086 A | 12/1989 | Miura |
| 4,936,934 A | 6/1990 | Buehning |
| 4,944,879 A | 7/1990 | Steuck |
| 4,968,733 A | 11/1990 | Muller et al. |
| 4,981,730 A | 1/1991 | Zaleski |
| 4,985,298 A | 1/1991 | Buckley et al. |
| 5,006,247 A | 4/1991 | Dennison et al. |
| 5,061,751 A | 10/1991 | Patton |
| 5,064,866 A | 11/1991 | Toyomoto et al. |
| 5,071,880 A | 12/1991 | Sugo et al. |
| 5,075,342 A | 12/1991 | Ishigaki et al. |
| 5,120,594 A | 6/1992 | Mrozinski |
| 5,160,627 A | 11/1992 | Cussler et al. |
| 5,180,492 A | 1/1993 | Ohnishi et al. |
| 5,200,471 A | 4/1993 | Coleman et al. |
| 5,202,025 A | 4/1993 | Onishi et al. |
| 5,209,849 A | 5/1993 | Hu et al. |
| 5,229,172 A | 7/1993 | Cahalan et al. |
| 5,260,360 A | 11/1993 | Mrozinski et al. |
| 5,282,971 A | 2/1994 | Degen et al. |
| 5,290,871 A | 3/1994 | Ahmed et al. |
| 5,308,641 A | 5/1994 | Cahalan et al. |
| 5,336,698 A | 8/1994 | Kashiwagi et al. |
| 5,342,688 A | 8/1994 | Kitchin et al. |
| 5,344,701 A | 9/1994 | Gagnon et al. |
| 5,350,805 A | 9/1994 | Lin |
| 5,429,629 A | 7/1995 | Latimer |
| 5,439,983 A | 8/1995 | Ahmed et al. |
| 5,453,467 A | 9/1995 | Bamford et al. |
| 5,458,782 A | 10/1995 | Hou et al. |
| 5,503,746 A | 4/1996 | Gagnon |
| 5,506,279 A | 4/1996 | Babu et al. |
| 5,531,900 A | 7/1996 | Raghavan et al. |
| 5,547,576 A | 8/1996 | Onishi et al. |
| 5,578,400 A | 11/1996 | Gineste et al. |
| 5,589,269 A | 12/1996 | Ali et al. |
| 5,623,044 A | 4/1997 | Chiao |
| 5,627,217 A | 5/1997 | Rilling et al. |
| 5,648,400 A | 7/1997 | Sugo et al. |
| 5,652,050 A | 7/1997 | Pall et al. |
| 5,712,027 A | 1/1998 | Ali et al. |
| 5,736,051 A | 4/1998 | Degen et al. |
| 5,773,485 A | 6/1998 | Bennett et al. |
| 5,782,908 A | 7/1998 | Cahalan et al. |
| 5,804,263 A | 9/1998 | Goldberg et al. |
| 5,846,438 A | 12/1998 | Pall et al. |
| 5,871,823 A | 2/1999 | Anders et al. |
| 5,902,836 A | 5/1999 | Bennett et al. |
| 5,906,734 A | 5/1999 | Girot et al. |
| 5,914,182 A | 6/1999 | Drumheller |
| 5,962,544 A | 10/1999 | Waller, Jr. |
| 6,033,719 A | 3/2000 | Keogh |
| 6,039,872 A | 3/2000 | Wu et al. |
| 6,056,529 A | 5/2000 | Meyering et al. |
| 6,063,484 A | 5/2000 | Exsted et al. |
| 6,096,293 A | 8/2000 | Stringer et al. |
| 6,096,369 A | 8/2000 | Anders et al. |
| 6,207,749 B1 | 3/2001 | Mayes |
| 6,230,776 B1 | 5/2001 | Choi |
| 6,245,922 B1 | 6/2001 | Heilmann et al. |
| 6,258,276 B1 | 7/2001 | Mika et al. |
| 6,264,044 B1 | 7/2001 | Meyering et al. |
| 6,267,916 B1 | 7/2001 | Meyering et al. |
| 6,280,853 B1 | 8/2001 | Mickols |
| 6,287,730 B1 | 9/2001 | Callahan et al. |
| 6,315,130 B1 | 11/2001 | Olsen |
| 6,387,379 B1 | 5/2002 | Goldberg et al. |
| 6,391,200 B2 | 5/2002 | Pulek et al. |
| 6,413,070 B1 | 7/2002 | Meyering et al. |
| 6,448,301 B1 | 9/2002 | Gaddam et al. |
| 6,458,269 B1 | 10/2002 | Bassett et al. |
| 6,464,084 B2 | 10/2002 | Pulek |
| 6,506,847 B1 | 1/2003 | Song |
| 6,511,600 B1 | 1/2003 | Ohtani |
| 6,513,666 B2 | 2/2003 | Meyering et al. |
| 6,521,011 B1 | 2/2003 | Sundet et al. |
| 6,537,411 B1 | 3/2003 | Kang et al. |
| 6,596,167 B2 | 7/2003 | Ji et al. |
| 6,635,104 B2 | 10/2003 | Komkova et al. |
| 6,660,376 B1 | 12/2003 | Zimmel et al. |
| 6,669,994 B2 | 12/2003 | Swan et al. |
| 6,712,966 B1 | 3/2004 | Pulek et al. |
| 6,743,878 B2 | 6/2004 | Bowers et al. |
| 6,773,654 B2 | 8/2004 | Sugo et al. |
| 6,776,940 B2 | 8/2004 | Meyering et al. |
| 6,811,837 B2 | 11/2004 | Iwasa et al. |
| 6,818,038 B2 | 11/2004 | Sugo et al. |
| 6,828,386 B2 | 12/2004 | MacKinnon |
| 6,844,371 B1 | 1/2005 | Komatsu et al. |
| 6,852,802 B1 | 2/2005 | Komatsu et al. |
| 6,861,001 B2 | 3/2005 | Lee et al. |
| 6,939,466 B2 | 9/2005 | Pulek et al. |
| 7,048,855 B2 | 5/2006 | de la Cruz |
| 7,067,058 B2 | 6/2006 | Yeh et al. |
| 7,073,671 B2 | 7/2006 | Charkoudian |
| 7,094,469 B2 | 8/2006 | Moya |
| 7,112,389 B1 | 9/2006 | Arora et al. |
| 7,125,603 B2 | 10/2006 | David et al. |
| RE39,399 E | 11/2006 | Allen |
| 7,135,230 B2 | 11/2006 | Nakao et al. |
| 7,160,464 B2 | 1/2007 | Lee et al. |
| 7,169,933 B2 | 1/2007 | Benson et al. |
| 7,170,739 B1 | 1/2007 | Arora et al. |
| 7,178,676 B2 | 2/2007 | Pulek et al. |
| 7,204,997 B2 | 4/2007 | Bromberg et al. |
| 7,235,122 B2 | 6/2007 | Bryner et al. |
| 7,247,370 B2 | 7/2007 | Childs et al. |
| 7,294,743 B2 | 11/2007 | Algotsson et al. |
| 7,316,919 B2 | 1/2008 | Childs et al. |
| 7,338,692 B2 | 3/2008 | Smith et al. |
| 7,361,767 B2 | 4/2008 | Benson et al. |
| 7,374,416 B2 | 5/2008 | Cook et al. |
| 7,402,678 B2 | 7/2008 | Benson et al. |
| 7,604,746 B2 | 10/2009 | Childs et al. |
| 2002/0001834 A1 | 1/2002 | Keogh |
| 2003/0134551 A1 | 7/2003 | Sugo |
| 2004/0116026 A1 | 6/2004 | Kubose et al. |
| 2004/0116028 A1 | 6/2004 | Bryner |
| 2004/0203149 A1 | 10/2004 | Childs et al. |
| 2004/0242714 A1 | 12/2004 | Penezina et al. |
| 2005/0025911 A1 | 2/2005 | Kasperchik |
| 2005/0058821 A1 | 3/2005 | Smith et al. |
| 2005/0095266 A1 | 5/2005 | Perichaud et al. |
| 2005/0118425 A1 | 6/2005 | Childs et al. |
| 2005/0133441 A1 | 6/2005 | Charkoudian |
| 2005/0142296 A1 | 6/2005 | Lakshmi |
| 2005/0165167 A1 | 7/2005 | MacKinnon |
| 2005/0199335 A1 | 9/2005 | Oehl et al. |
| 2006/0016748 A1 | 1/2006 | Koguma et al. |
| 2006/0023487 A1 | 2/2006 | Fang et al. |
| 2006/0107639 A1 | 5/2006 | Hamlin et al. |
| 2006/0121217 A1 | 6/2006 | Childs et al. |
| 2006/0165999 A1 | 7/2006 | Fansler |
| 2006/0178070 A1 | 8/2006 | Kritzer et al. |
| 2007/0039874 A1 | 2/2007 | Kniajanski et al. |
| 2007/0042015 A1 | 2/2007 | Berry et al. |

(56) References Cited

U.S. PATENT DOCUMENTS

| | | | |
|---|---|---|---|
| 2007/0065490 | A1 | 3/2007 | Schabert et al. |
| 2007/0138084 | A1 | 6/2007 | Galvin |
| 2007/0154651 | A1 | 7/2007 | Weiss et al. |
| 2007/0154703 | A1 | 7/2007 | Waller et al. |
| 2007/0221569 | A1 | 9/2007 | Stouffer et al. |
| 2008/0017578 | A1 | 1/2008 | Childs et al. |
| 2008/0230471 | A1 | 9/2008 | Tamada et al. |
| 2008/0264867 | A1 | 10/2008 | Mika et al. |
| 2009/0020472 | A1 | 1/2009 | Lucas et al. |
| 2009/0032463 | A1 | 2/2009 | Childs et al. |
| 2009/0035552 | A1 | 2/2009 | Childs et al. |
| 2009/0098359 | A1 | 4/2009 | Waller, Jr. et al. |
| 2009/0176052 | A1 | 7/2009 | Childs et al. |
| 2010/0075131 | A1 | 3/2010 | Seshadri et al. |
| 2010/0075560 | A1 | 3/2010 | Seshadri et al. |

FOREIGN PATENT DOCUMENTS

| | | |
|---|---|---|
| EP | 0 779 387 | 6/1997 |
| EP | 0 860 213 | 8/1998 |
| EP | 1 228 756 | 8/2002 |
| EP | 1 552 878 | 7/2005 |
| EP | 2027921 | 2/2009 |
| EP | 2 036 930 | 3/2009 |
| JP | 62298405 | 12/1987 |
| JP | 63240902 | 10/1988 |
| JP | 5111607 | 5/1993 |
| JP | 08290066 | 11/1996 |
| JP | 10085572 | 4/1998 |
| JP | 10279713 | 10/1998 |
| JP | 2002371471 | 12/2002 |
| JP | 2003301059 | 10/2003 |
| JP | 2004073943 | 3/2004 |
| WO | WO 89/09246 | 10/1989 |
| WO | WO 97/18904 | 5/1997 |
| WO | WO 00/01468 | 1/2000 |
| WO | WO 00/22032 | 4/2000 |
| WO | WO 00/54866 | 9/2000 |
| WO | WO 01/96487 | 12/2001 |
| WO | WO 02/060509 | 8/2002 |
| WO | WO 03/008011 | 1/2003 |
| WO | WO 03/055923 | 7/2003 |
| WO | WO 2004/002714 | 1/2004 |
| WO | WO 2005/035641 | 4/2005 |
| WO | WO 2005/040092 | 5/2005 |
| WO | WO 2007/001405 | 1/2007 |
| WO | WO 2007/078878 | 7/2007 |
| WO | WO 2007/078880 | 7/2007 |
| WO | WO 2008/008872 | 1/2008 |
| WO | WO 2009/085726 | 7/2009 |
| WO | WO 2009/086347 | 7/2009 |
| WO | WO 2009/127285 | 10/2009 |
| WO | WO 2009/146321 | 12/2009 |
| WO | WO 2009/148869 | 12/2009 |
| WO | WO 2010/033794 | 3/2010 |

OTHER PUBLICATIONS

European Search Report, EP Application No. 12172504, dated Oct. 15, 2012.

U.S. Appl. No. 61/057,517 entitled, "Method of Making Ligand Functionalized Substrates" filed May 30, 2008.

U.S. Appl. No. 61/057,523 entitled, "Ligand Functionalized Substrates" filed May 30, 2008.

U.S. Appl. No. 12/819,261 entitled, "Funtionalized Nonwoven Article" filed Jun. 21, 2010.

Barner, L., et al., "Reversible Addition-Fragmentation Chain Transfer Graft Copolymerization of Styrene and m-Isopropenyl-α, α'-dimethylbenzyl Isocyanate from Polypropylene Lanterns: Solid Phases for Scavenging Applications." Journal of Polymer Science: Part A: Polymer Chemistry, vol. 44, 2006, pp. 857-864.

Barsbay, M. et al., "Verification of Controlled Grafting of Styrene from Cellulose via Radiation-Induced RAFT Polymerization," Macromolecules, vol. 40, No. 20, 2007, pp. 7140-7147.

Buehler et al., "Solvent Effects on the Permeability of Membrane-Supported Gels," Ind. Eng. Chem. Res., vol. 41, No. 3, pp. 464-472, (2002).

Burke, J., "Solubility Parameters: Theory and Application," AIC Book and Paper Group Annual, vol. 3, (1984), pp. 13-58.

Chen, J., et al., "Grafting copolymerization of acrylamides onto preirradiated PP Films," Radiation Physics and Chemistry, vol. 55, (1999), pp. 87-92.

Childs, et al., "Nanofiltration using pore-filled membranes: effect of polyelectrolyte composition on performance", Separation and Purification Technology; 22-23 (2001), pp. 507-517.

Davies, "The Separation of Airborne Dust and Particles," the Institution of Mechanical Engineers, Proceedings (B), vol. 1B, Nos. 1-12, pp. 185-213, (1952-1953).

DuPont™ brochure entitled, "DuPont™ Hybrid Membrane Technology—Nanofiber Science to Revolutionize Filtration, Energy Storage and Beyond," Copyright © 2007, 4 pages.

Franken, A. et al., "Wetting Criteria for the Applicability of Membrane Distillation," Journal of Membrane Science, vol. 33, (1987), pp. 315-328.

Ghosh, "Protein separation using membrane chromatography: opportunities and challenges," Journal of Chromatography A., vol. 952, Issues 1-2, pp. 13-27, Apr. 5, 2002.

Grasselli, M. et al., "Electron-beam induced RAFT-graft polymerization of poly(acrylic acid) onto PVDF," Nuclear Instruments and Methods in Physics Research B, vol. 236, 2005, pp. 202-207.

Gupta, B., et al., Preirradiation grafting of acrylonitrile onto polypropylene monofilament for biomedical applications: I. Influence of synthesis conditions, Radiation Physics and Chemistry, vol. 75, (2006), pp. 161-167.

Ito, et al., "pH-Sensitive Gating by Conformational Change of a Polypeptide Brush Grafted onto a Porous Polymer Membrane," Journal of the American Chemical Society, vol. 119, pp. 1619-1623, (1997).

Jianqin, L., et al., "Pre-irradiation grafting of temperature sensitive hydrogel on cotton cellulose fabric," Radiation Physics and Chemistry, vol. 55, (1999), pp. 55-59.

Kanani et al., "Separation of human plasma proteins HAS and HIgG using high-capacity macroporous gel-filled membranes," Biochemical Engineering Journal, vol. 35, pp. 295-300, (2007).

Kanani, et al., "Protein bioseparation by membrane chromatography using polyelectrolyte gel-coated adsorptive membranes," Department of Chemical Engineering, McMaster University, 7 pages, (2004).

Kavakli, et al., "Radiation-induced grafting of dimethylaminoethylmethacrylate onto PE/PP nonwoven fabric," Science Direct, Nuclear Instruments and Methods in Physics Research B, vol. 265, pp. 204-207, (2007).

Kawai et al., "Protein binding to polymer brush, based on ion-exchange, hydrophobic, and affinity interactions," Journal of Chromatography B, vol. 790, Issues 1-2, pp. 131-142, Jun. 25, 2003.

Kiani, K., et al., "Raft Mediated Surface Grafting of t-Butyl Acrylate onto an Ethylene-Propylene Copolymer Initiated by Gamma-Radiation," Journal of Polymer Science: Part A: Polymer Chemistry, vol. 45, 2007, pp. 1074-1083.

Kim et al., "Diffusion and Flow through Polymer-Lined Micropores," Ind. Eng. Chem. Res., vol. 30, pp. 1008-1016, (1991).

Latulippe, et al., "Characterization of Gel-Filled Membranes for Plasma Protein Fractionation," Department of Chemical Engineering, McMaster University, 4 pages, (2004).

Mika et al., "Acid/base properties of poly(4-vinylpyridine) anchored within microporous membranes," Journal of Membrane Science, vol. 152, pp. 129-140, (1999).

Mika et al., "Chemical valves based on poly(4-vinylpyridine)-filled microporous membranes," Journal of Membrane Science, vol. 153, pp. 45-56, (1999).

Mika et al., "Porous, polyelectrolyte-filled membranes: Effect of cross-linking on flux and separation", Journal of Membrane Science, 135 (1997), pp. 81-92.

Mika et al., "Salt separation and hydrodynamic permeability of porous membrane filled with pH-sensitive gel," Journal of Membrane Science, vol. 206, pp. 19-30, (2002).

(56) References Cited

OTHER PUBLICATIONS

Mika, et al., "A new class of polyelectrolyte-filled microfiltration membranes with environmentally controlled porosity", Journal of Membrane Science, 108 (1995) pp. 37-56.

Mika, et al., "Poly(4-vinylpyridine)-filled microfiltration membranes: physicochemical properties and morphology", Journal of Membrane Science, 136 (1997), pp. 221-232.

Nho, Y., et al., "Grafting polymerization of styrene onto preirradiated polypropylene fabric," Radiation and Physics and Chemistry, vol. 54, (1999), pp. 317-322.

Osada et al., "Control of Water Permeability by Mechanochemical Contraction of Poly(Methacrylic Acid)-Grafted Membranes," Journal of Membrane Science, vol. 27, pp. 327-338, (1986).

Pietrucha, K., "Effect of Chain Transfer Agent on the Radiation Grafting of Methyl Methacrylate Onto Chromium (III) Crosslinked Collagen," Journal of Radioanalytical and Nuclear Chemistry, vol. 149, No. 2, (1991), pp. 327-331.

Shaozao, T., et al., "Effect of Gamma Ray Irradiation on Properties of Polypropylene Fibers and Nonwoven Fabrics," vol. 22, No. 6, (1999), pp. 18-21.

Suryanarayan et al., "The effect of gel layer thickness on the salt rejection performance of polyelectrolyte gel-filled nanofiltration membranes," Journal of Membrane Science, vol. 290, pp. 196-206, (2007).

Ulbricht et al., "Porous Polypropylene Membranes with Different Carboxyl Polymer Brush Layers for Reversible Protein Binding via Surface-Initiated Graft Copolymerization," Chem. Mater, vol. 17, No. 10, pp. 2622-2631, (2005).

Ulbricht, "Advanced functional polymer membranes," Polymer, vol. 47, pp. 2217-2262, (2007).

Wente et al., "Manufacture of Superfine Organic Fibers," Navel Research Laboratories Report No. 4364, (1954).

Wente, "Superfine Thermoplastic Fibers," Industrial and Engineering Chemistry, Naval Research Laboratory, vol. 48, No. 8, pp. 1342-1346, (1956).

Winnik et al., "Polyacrylic acid pore-filled microporous membranes and their use in membrane-mediated synthesis of nanocrystalline ferrihydrite," Can. J. Chem., vol. 76, pp. 10-17, (1998).

Zazzera et al., "XPS and SIMS Study of Anhydrous HF and UV/Ozone-Modified Silicon (100) Surfaces," J. Electrochem. Soc., vol. 136, No. 2, (1989), pp. 484-491.

Zhang et al., "pH Control of Transport through a Porous Membrane Self-Assembled with a Poly(acrylic acid) Loop Brush," Langmuir, vol. 17, pp. 8336-8340, (2001).

Zhou et al., "Pore-filled nanofiltration membranes based on poly(2-acrylamido-2-methylpropanesulfonic acid) gels," Journal of Membrane Science, vol. 254, pp. 89-99, (2005).

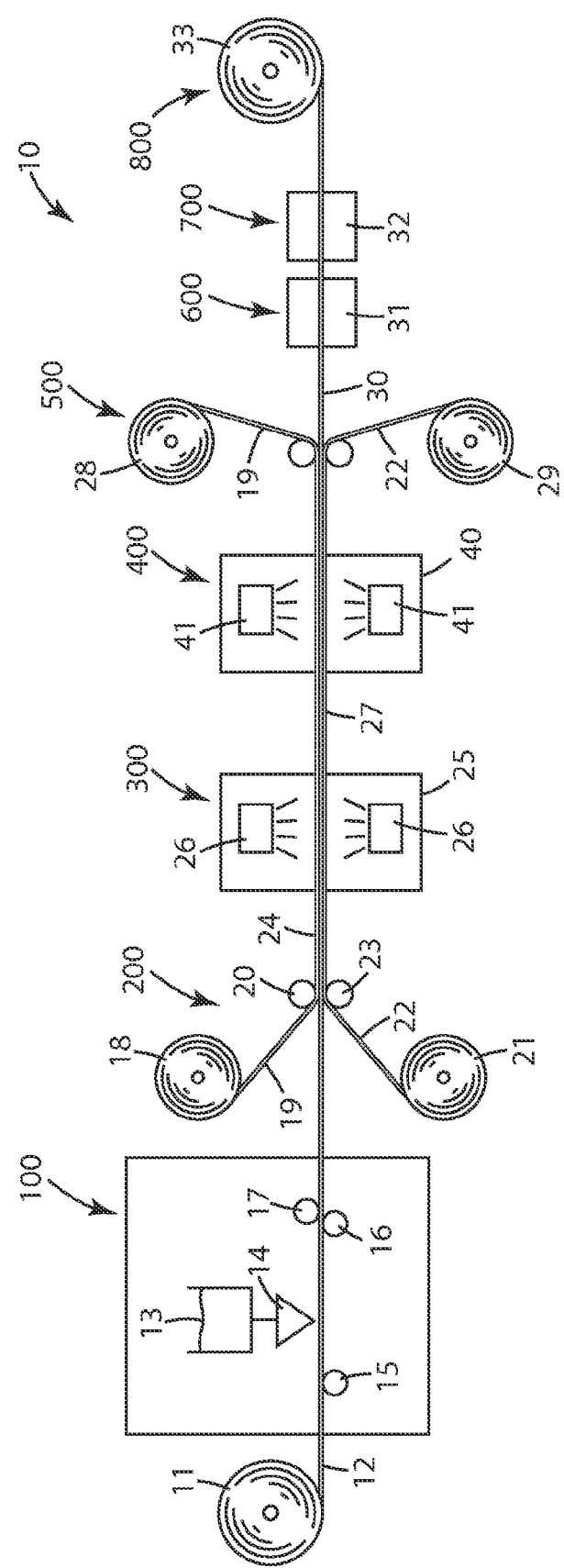

METHOD OF MAKING LIGAND FUNCTIONALIZED SUBSTRATES

CROSS-REFERENCE TO RELATED APPLICATIONS

This application is a national stage filing under 35 U.S.C. 371 of PCT/US2009/045110, filed May 26, 2009, which claims priority to Provisional Application No. 61/057,517, filed May 30, 2008, the disclosure of which is incorporated by reference in its/their entirety herein.

TECHNICAL FIELD

The present disclosure relates to ligand-functionalized substrates, and methods for preparing the same. The functionalized substrates are useful in selectively binding and removing biological materials, such as viruses, from biological samples.

BACKGROUND

Detection, quantification, isolation and purification of target biomaterials, such as viruses and biomacromolecules (including constituents or products of living cells, for example, proteins, carbohydrates, lipids, and nucleic acids) have long been objectives of investigators. Detection and quantification are important diagnostically, for example, as indicators of various physiological conditions such as diseases. Isolation and purification of biomacromolecules are important for therapeutic and in biomedical research. Biomacromolecules such as enzymes which are a special class of proteins capable of catalyzing chemical reactions are also useful industrially; enzymes have been isolated, purified, and then utilized for the production of sweeteners, antibiotics, and a variety of organic compounds such as ethanol, acetic acid, lysine, aspartic acid, and biologically useful products such as antibodies and steroids.

In their native state in vivo, structures and corresponding biological activities of these biomacromolecules are maintained generally within fairly narrow ranges of pH and ionic strength. Consequently, any separation and purification operation must take such factors into account in order for the resultant processed biomacromolecule to have potency.

Chromatographic separation and purification operations can be performed on biological product mixtures, based on the interchange of a solute between a moving phase, which can be a gas or liquid, and a stationary phase. Separation of various solutes of the solution mixture is accomplished because of varying binding interactions of each solute with the stationary phase; stronger binding interactions generally result in longer retention times when subjected to the dissociation or displacement effects of as mobile phase compared to solutes which interact less strongly and, in this fashion, separation and purification can be effected.

Most current capture or purification chromatography is done via conventional column techniques. These techniques have severe bottlenecking issues in downstream purification, as the throughput using this technology is low. Attempts to alleviate these issues include increasing the diameter of the chromatography column, but this in turn creates challenges due to difficulties of packing the columns effectively and reproducibly. Larger column diameters also increase the occurrence of problematic channeling. Also, in a conventional chromatographic column, the absorption operation is shut down when a breakthrough of the desired product above a specific level is detected. This causes the dynamic or effective capacity of the adsorption media to be significantly less than the overall or static capacity. This reduction in effectiveness has severe economic consequences, given the high cost of some chromatographic resins.

Polymeric resins are widely used for the separation and purification of various target compounds. For example, polymeric resins can be used to purify or separate a target compound based on the presence of an ionic group, based on the size of the target compound, based on a hydrophobic interaction, based on an affinity interaction, or based on the formation of a covalent bond. There is a need in the art for polymeric substrates having enhanced affinity for viruses to allow selective removal from a biological sample. There is further need in the art for ligand functionalized membranes that overcome limitations in diffusion and binding, and that may be operated at high throughput and at lower pressure drops.

SUMMARY OF THE INVENTION

The present invention is directed to ligand functionalized substrates, preferably porous substrates, and methods of making the same. More specifically, the functionalized substrates include a base substrate, preferably a porous base substrate, which has been modified to provide grafted ligand groups having the requisite affinity for binding neutral or negatively charged biomaterials, such as viruses. The ligand functionalized substrate may be described as the grafted reaction product of a substrate and a ligand monomer of Formula I:

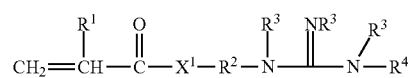

wherein
$R^1$ is H or $C_1$-$C_4$ alkyl;
$R^2$ is a divalent alkylene, preferably having 1 to 20 carbon atoms and optionally containing an ester, amide, urethane or urea linking group;
each $R^3$ is independently H or $C_1$-$C_4$ alkyl;
$R^4$ is H, $C_1$-$C_4$ alkyl or —$N(R^3)_2$; and $X^1$ is —O— or —$NR^3$—. The base substrate may be directly- or indirectly grafted with the ligand monomer of Formula I, as further described herein.

Methods of making a ligand functionalized substrate are provided. In some embodiments, the method comprises:
1) providing a base substrate;
2) coating the base substrate with a solution comprising: (a) at least one grafting monomer having an acryloyl group and a photoinitiator group ("photoinitiator monomer"); (b) one or more ligand monomers of Formula I, (c) optionally one or more monomers having at least one acryloyl group and at least one additional ethylenically unsaturated, free-radically polymerizable group; and (d) optionally one or more hydrophilic monomers;
3) exposing the coated base substrate to ionizing radiation, preferably e-beam or gamma radiation, to form a first functionalized substrate comprising grafted photoinitiator group attached to ate surface of the base substrate, and
4) exposing the base substrate comprising grafted photoinitiator groups to UV radiation to polymerize the remaining ethylenically unsaturated, free-radically polymerizable groups.

The term "ethylenically unsaturated group" refers to those groups having carbon-carbon double (or triple) bonds that may be free-radically polymerized, and includes (meth)acrylamides, (meth)acrylates, vinyl and vinyloxy groups, allyl and allyloxy groups, and acetylenic groups.

Preferably the substrate is a porous substrate having interstitial and outer surfaces wherein the step of coating the porous substrate comprises a first imbibing step with the photoinitiator monomer, followed by ionizing radiation exposure to produce a porous substrate having grafted photoinitiators thereon, followed by a second imbibing step with the ligand monomer, followed by UV polymerization to crosslink the remaining ethylenically unsaturated, free-radically polymerizable groups. Optional monomers may be added with the first imbibing step prior to ionizing radiation exposure, or may be added in a second imbibing step.

In another embodiment, the step of imbibing may include a first imbibing step with the photoinitiator monomer and the ligand monomer of Formula I, followed by ionizing radiation exposure, preferably e-beam or gamma radiation, to produce a porous substrate having grafted photoinitiator groups and grafted ligand groups, followed by UV polymerization to crosslink the remaining ethylenically unsaturated, free-radically polymerizable groups.

An article is provided comprising a porous substrate having interstitial and outer surfaces and grafted ligand groups extending from the surfaces thereof, said ligand groups of Formula II:

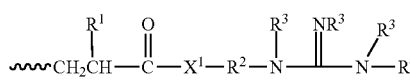

wherein
$R^1$ is H or $C_1$-$C_4$ alkyl;
$R^2$ is a divalent alkylene, preferably having 1 to 20 carbon atoms and optionally containing an ester, amide, urethane or urea linking group;
each $R^3$ is independently H or $C_1$-$C_4$ alkyl,
$R^4$ is H, $C_1$-$C_4$ alkyl or —$N(R^3)_2$; and
$X^1$ is —O— or —$NR^3$—.

With respect to the above Formula II, the "~" represents a covalent bond or an organic linking group interposed between the ligand group and the surface of the base substrate. The article may further comprise grafted poly(oxyalkylene) groups extending from the surfaces of the substrate, and may comprise grafted ethylenically unsaturated polymerizable groups extending from the surface of the substrate, which is preferably porous.

The article may comprise the further reaction product, upon grafting by exposure to ionizing radiation (preferably e-beam or gamma radiation) and UV irradiation, of (c) monomers having at least one acryloyl group and at least one additional ethylenically unsaturated, free-radically polymerizable group and optionally d) monomers having at least one ethylenically unsaturated, free-radically polymerizable group and a hydrophilic group. Any free ethylenically unsaturated groups that remain ungrafted to the base substrate after e-beam exposure may polymerize upon subsequent exposure to UV radiation and therefore indirectly grafted to the base substrate.

With respect to the method and article, all or a portion of the acryloyl groups of the photoinitiator monomer a) will be grafted to the surface of the base substrate upon ionizing irradiation. The unreacted photoinitiator monomers may be subsequently incorporated into the growing polymer chain on exposure to UV radiation. The remaining, b), c) and d) monomers may be directly grafted to the surfaces (for example by wafting of an acryloyl group), or indirectly grafted by incorporation into the growing polymer chain on exposure to UV radiation.

These and other features and advantages of the present invention will become apparent after a review of the following detailed description of the disclosed embodiments and the appended claims.

BRIEF DESCRIPTION OF THE DRAWINGS

FIG. 1 depicts exemplary method steps for making ligand-functionalized porous articles of the present invention.

DETAILED DESCRIPTION OF THE INVENTION

In the article and methods of this invention, ligand-functionalized articles are provided by a two-step process of grafting of monomers (such as by e-beam grafting) and subsequent UV crosslinking of free, ungrafted ethylenically unsaturated polymerizable groups. Compared to the porous base substrate before surface modification, the ligand functionalized substrate typically has enhanced affinity for neutral or negatively charged biological materials such as host cell proteins, DNA, RNA and viruses. The affinity for such biomaterials allows positively charged materials, such as antibodies to be purified, as they are not bound to the ligand functional groups. The ligand functionalized substrate allows the selective capture or binding of target biomaterials by the ligand groups, while other materials, lacking the affinity for the ligand groups are passed.

The ligand functionalized substrate comprises a number of components including, but not limited to, (1) a base substrate and (2) the UV initiated reaction product of a) a grafted photoinitiator group extending from the surfaces of the base substrate, with (b) one or more ligand monomers of Formula II, c) optionally one or more monomers having at least one acryloyl group and at least one additional free-radically polymerizable group and (d) optionally one or more hydrophilic monomers. Preferably the base substrate is as porous base substrate having interstitial and outer surfaces. As used herein, the term "acryloyl" refers to acrylate and acrylamide groups, and the term "(meth)acryloyl" refers to acryloyl and methacryloyl groups.

The base substrate may be formed from any suitable thermoplastic polymeric material. Suitable polymeric materials include, but are not limited to, polyolefins, poly(isoprenes), poly(butadienes), fluorinated polymers, chlorinated polymers, is polyamides, polyimides, polyethers, poly(ether sulfones), poly(sulfones), poly(vinyl acetates), copolymers of vinyl acetate, such as poly(ethylene)-co-poly(vinyl alcohol), poly(phosphazenes), poly(vinyl esters), poly(vinyl ethers), poly(vinyl alcohols), and poly(carbonates).

Suitable polyolefins include, but are not limited to, poly (ethylene), poly(propylene), poly(1-butene), copolymers of ethylene and propylene, alpha olefin copolymers (such as copolymers of ethylene or propylene with 1-butene, 1-hexene, 1-octene, and 1-decene), poly(ethylene-co-1-butene) and poly(ethylene-co-1-butene-co-1-hexene).

Suitable fluorinated polymers include, but are not limited to, poly(vinyl fluoride), poly(vinylidene fluoride), copolymers of vinylidene fluoride (such as poly(vinylidene fluoride-co-hexafluoropropylene), and copolymers of chlorotrifluoroethylene (such as poly(ethylene-co-chlorotrifluoroethylene).

Suitable polyamides include, but are not limited to, poly (iminoadipoyliminohexamethylene), poly(iminoadipoyliminodecamethylene), and polycaprolactam. Suitable polyimides include, but are not limited to, poly(pyromellitimide).

Suitable poly(ether sulfones) include, but are not limited to, poly(diphenylether sulfone) and poly(diphenylsulfone-co-diphenylene oxide sulfone).

Suitable copolymers of vinyl acetate include, but are not limited to, poly(ethylene-co-vinyl acetate) and such copolymers in which at least some of the acetate groups have been hydrolyzed to afford various poly(vinyl alcohols).

The base substrate may be in any form such as films or sheets. Preferably the base substrate is porous. Suitable porous base substrates include, but are not limited to, porous membranes, porous nonwoven webs, and porous fibers.

In some embodiments, the porous base substrate is formed from a propylene homo- or copolymers, most preferably propylene homopolymers. Polypropylene polymers are often a material of choice for porous articles, such as nonwovens and microporous films, due to properties such as non-toxicity, inertness, low cost, and the ease with which it can be extruded, molded; and formed into articles. However, polypropylene is hydrophobic. While it is desirable to render polymers such as polypropylene ligand functionalized, polypropylene treated with ionizing radiation is subject to degradation, e.g., embrittlement, discoloration, and thermal sensitivity, during or subsequent to irradiation, which therefore limits the ability to render such thermoplastic polymers ligand functionalized by e-beam grafting.

For radiation sensitive substrates, such as polypropylene, the present invention overcomes such polymer degradation by rising a low dose of ionizing radiation preferably e-beam or gamma radiation, to graft photoinitiator groups and optionally grafting other monomers on a portion of the surface, then polymerizing or crosslinking, any ungrafted, unreacted ethylenically unsaturated groups by UV radiation.

In many embodiments, the porous base substrate has an average pore site that is typically greater than about 0.2 micrometers in order to minimize size exclusion separations, minimize diffusion constraints and maximize surface area and separation based on binding of a target molecule. Generally, the pore size is in the range of 0.1 to 10 micrometers, preferably 0.5 to 3 micrometers and most preferably 0.8 to 2 micrometers when used for binding of viruses. The efficiency of binding other target molecules may confer different optimal ranges.

Suitable porous base substrates include, but are not limited to, porous and microporous membranes, nonwoven webs, and fibers. In some embodiments, the porous base substrate is a microporous membrane such as a thermally-induced phase separation (TIPS) membrane. TIPS membranes are often prepared by forming a homogenous solution of a thermoplastic material and a second material above the melting point of the thermoplastic material. Upon cooling, the thermoplastic material crystallizes and phase separates from the second material. The crystallized thermoplastic material is often stretched. The second material is optionally removed either before or after stretching. Microporous membrane are further disclosed in U.S. Pat. Nos. 4,539,256 (Shipman), 4,726,989 (Mrozinski), 4,867,881 (Kinzer), 5,120,594 (Mrozinski), 5,260,360 (Mrozinski et al.), and 5,962,544 (Waller), all of which are assigned to 3M Company (St. Paul, Minn.). Further, the microporous film can be prepared from ethylene-vinyl alcohol copolymers as described in U.S. Pat. No. 5,962,544 (Waller).

Some exemplary TIPS membrane comprise poly(vinylidene fluoride) (PVDF), polyolefins such as polyethylene homo- or copolymers or polypropylene homo- or copolymers, vinyl-containing polymers or copolymers such as ethylene-vinyl alcohol copolymers and butadiene-containing polymers or copolymers, and acrylate-containing polymers or copolymers. For some applications, a TIPS membrane comprising PVDF is particularly desirable. TIPS membranes comprising PVDF are further described in U.S. Pat. No. 7,338,692 (Smith et al.).

In another exemplary embodiment the porous bases substrate comprises a nylon microporous film or sheet, such as those described in U.S. Pat. Nos. 6,056,529 (Meyering et al.), 6,267,916 (Meyering et al.), 6,413,070 (Meyering et al.), 6,776,940 (Meyering et al.), 3,876,738 (Marinacchio et al.), 3,928,517, 4,707,265 (Knight et al.), and 5,458,782 (Hou et al.).

In other embodiments, the porous base substrate is a nonwoven web which may include nonwoven webs manufactured by any of the commonly known processes for producing nonwoven webs. As used herein, the term "nonwoven web" refers to a fabric that has a structure of individual fibers or filaments which are randomly and/or unidirectionally interlaid in as mat-like fashion.

For example, the fibrous nonwoven web can be made by carded, air laid, spunlaced, spunbonding or melt-blowing techniques or combinations thereof. Spunbonded fibers are typically small diameter fibers that are firmed by extruding molten thermoplastic polymer as filaments from a plurality of fine, usually circular capillaries of a spinneret with the diameter of the extruded fibers being rapidly reduced. Meltblown fibers are typically formed by extruding the molten thermoplastic material through a plurality of fine, usually circular, die capillaries as molten threads or filaments into a high velocity, usually heated gas (e.g. air) stream which attenuates the filaments of molten thermoplastic material to reduce their diameter. Thereafter, the meltblown fibers are carried by the high velocity gas stream and are deposited on a collecting surface to from a web of randomly disbursed meltblown fibers. Any of the non-woven webs may be made from a single type of fiber or two or more fibers that differ in the type of thermoplastic polymer and/or thickness.

Further details on the manufacturing method of non-woven webs of this invention may be found in Wente, Superfine Thermoplastic Fibers, 48 INDUS. ENG. CHEM. 1342 (1956), or in Wente et al., Manufacture Of Superfine Organic Fibers, (Naval Research Laboratories Report No. 4364, 1954).

The functionalized substrate has grafted groups attached to the surfaces of the base substrate which includes a) at least one photoinitiator group (or the reaction product thereof), with (b) one or more ligand monomers, c) optionally one or more monomers having at least one acryloyl group and at least one additional free-radically polymerizable group and (d) optionally uric or more hydrophilic monomers.

The monomers that are grafted to the surface of the base substrates usually have both (a) an acryloyl group for grafting by e-beam and b) at least one additional function group thereon, which includes a) a photoinitiator group to initiate the polymerization on exposure to UV radiation, b) a ligand group derived from monomers of Formula II, optionally c) a (meth)acryloyl or a non-(meth)acryloyl, free-radically polymerizable ethylenically unsaturated group for subsequent polymerization derived from the "c)" monomers and optionally d) a hydrophilic group, including ionic groups derived from the "d)" monomers.

Acryloyl groups, including acrylate and acrylamide groups are preferred for direct grafting of the monomer to the substrate surface due to the greater reactivity of such acryloyl groups on exposure to ionizing radiation, such as e-beam irradiation. However, not all such acryloyl groups may be "directly grafted", i.e. forming a covalent bond with the substrate surface. Some may remain free, and are subsequently "indirectly grafted" by incorporation into the polymer chain on exposure to UV radiation. Other ethylenically unsaturated groups, such as methacrylamides, methacrylates, vinyl and vinyloxy groups, allyl and allyloxy groups, and acetylenic groups are less reactive during e-beam grafting, and are less likely to be directly grafted to the base substrate. Therefore a portion of such non-acryloyl groups may be directly grafted, but largely remain unreacted, and are indirectly grafted to the substrate by incorporation into the polymer chain during UV initiated polymerization.

The photoinitiator "a)" monomers may be directly grafted onto surface of the base substrate, including the interstitial and outer surfaces of the porous base substrate to provide the requisite grafted photoinitiator group via the acryloyl group. The ligand "b)" monomers (of Formula I) may have an acryloyl group for direct grafting or a non-acryloyl group, such as a methacrylate group, for subsequent incorporation (indirect grafting) into the polymer chain during UV initiated polymerization. In addition to an acryloyl group, the free-radically polymerizable groups of monomer "c)" are typically other ethylenically unsaturated groups such as a methacrylamides, methacrylates, vinyl groups and acetylenic groups having reduced reactivity during grafting, and are therefore free and unreacted for the subsequent UV initiated polymerization and crosslinking.

The acryloyl group of the "c)" monomers typically can directly graft (i.e. forming a covalent bond) to the surface of the base substrate when exposed to an ionizing radiation preferably e-beam or gamma radiation. That is, reaction of acryloyl groups of the c) monomers with the surface of the porous base substrate in the presence of the electron beam results in the reaction of ethylenically unsaturated free-radically polymerizable groups directly grafted to the base substrate via the acrylate group.

A fourth grafting hydrophilic monomer "d)" may also be grafted via an acryloyl group, and may provide hydrophilic groups or ionic groups to the surfaces of the base substrate. In some embodiments, hydrophilic monomers having an ionic group may be directly or indirectly grafted to the substrate surface to provide secondary ionic interaction of the functionalized substrate. For example, ionic groups may be selected to have a positive charge (at a selected pH) to retard or repel various biomaterials from the substrate surface. In other embodiments the fourth monomer may have an ethylenically unsaturated group of reduced reactivity during the grafting step, but is subsequently incorporated by free-radical polymerization during the UV curing step (indirectly grafted).

The grafting photoinitiator monomers include an acryloyl group and a photoinitiator group, which may be a hydrogen-abstracting type or an α-cleavage-type photoinitiator group, and may be represented by the formula:

$$\overset{H}{\underset{}{\Big|}}\!\!=\!\!\overset{O}{\underset{}{\Big\|}}\!\!-X^1-R^6-PI \qquad III$$

where;
$X^1$ is —O— or —NR$^3$,
$R^3$ is independently H or $C_1$-$C_4$ alkyl;
$R^6$ is a divalent linking group connecting the acrylate group with the PI group; and PI is a photoinitiator represented by the structure:

$$-\!\!\bigcirc\!\!-\overset{O}{\underset{}{\overset{\|}{C}}}\!-R^8 \qquad$$

XII, wherein $R^8$ is $-\!\!\bigcirc\!\!\!\!-R^7 \quad -\!\!\bigcirc\!\!\!\!-R^7 \quad -N\!\!\bigcirc\!\!\!\!-R^7$ $-N\!\!\bigcirc\!\!\!\!N-R^7 \quad -N\!\!\bigcirc\!\!\!\!O-R^7 \quad \text{and} \quad -\overset{R^9}{\underset{R^9}{\overset{|}{\underset{|}{C}}}}-R^9$ wherein $R^7$ is H or a $C_1$ to $C_4$ alkyl group,
each $R^9$ is independently a hydroxyl group, a phenyl group, a $C_1$ to $C_6$ alkyl group, or a $C_1$ to $C_6$ alkoxy group. Such photoinitiator monomers are described, for example, in U.S. Pat. Nos. 5,902,836 (Babu et al.) and 5,506,279 (Babu et al.). Further details regarding the linking $R^6$ group may be found with reference to the method of preparing the photoinitiator grating monomer herein, and in the cited references.

In certain preferred embodiments, the photoinitiator monomers may be of the hydrogen-abstraction type represented by the general formula:

$$CH_2\!\!=\!\!CH\!-\!\!\left[\overset{O}{\underset{}{\overset{\|}{C}}}\!-X^1\!-\!(M^1)_a\!-\!(M^2)_b\!-\!(M^3)_c\!-\!\right]_p\!-G\!-\!PI^1 \qquad XIII$$

$X^1$ is O or NH;
p is 0 or 1;
o is 0 or an integer from 1 to 5;
a, b, and c are independently 0 or 1;
$M^1$ is $CH_2$ or $Si(R^1)_2$;
$M^2$ is $C(R^1)_2$ or $Si(R^1)_2$;
$M^3$ is —O—, —NH—, —C(O)—, —C(O)O—, —C(O)NH—, or —OC(O)NH—;
Each $R^1$ is independently H or a $C_1$ to $C_4$ alkyl group;
G is a covalent bond, —$(CH_2)_d$—, or —$(CH_2)_d$O— where d is an integer from 1 to 4, preferably from 1 to 2;
$PI^1$ is a radiation-sensitive hydrogen abstracting group having the general formula:

$$-\!\!\underset{R^{12}}{\overset{O}{\underset{}{\overset{\|}{Ar}}}}\!-R^{13} \qquad XIV$$

in which Ar is a substituted arene having 6 to 12 carbon atoms, preferably a benzenetriyl group;
$R^{12}$ is hydrogen, a $C_1$ to $C_{12}$ alkyl group, a $C_1$ to $C_{12}$ alkoxy group, or a phenyl group; and
$R^{13}$ is a $C_1$ to $C_6$ alkyl group, a cycloalkyl group having 3 to 14 carbon atoms, or

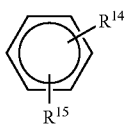

wherein $R^{14}$ and $R^{15}$ are independently selected from hydrogen, $C_1$ to $C_{12}$ alkyl groups, $C_1$ to $C_{12}$ alkoxy groups, and phenyl groups.

Included among those hydrogen abstracting photoinitiator monomers encompassed by Formula XIII are those where $PI^1$ is a moiety derived from one of the following compounds (or a substituted derivative thereof), the bond to is preferably located para to the bridging carbonyl group; benzopheneone, anthraquinone, 5,12-naphthacenequinone, aceanthracenequinone, benz(A)anthracene-7,12-dione, 1,4-chrysenequinone, 6,13-pentacenequinone, 5,7,12,14-pentacenetetrone, 9-fluorenone, anthrone, xanthone, thioxanthone, acridone, dibenzosuberone, acetophenone, and chromone. The synthesis of the formula XIII monomers is described in U.S. Pat. No. 5,773,485 (Bennett et al).

The weight percentage of the photoinitiator monomers of Formula XII or XIII in the imbibing solution(s) may be at least about 0.15%, and generally less than about 10%, relative to the total weight of other monomers (i.e. "b)", "c)", and "d)" monomers). It will be understood that all or a portion of the photoinitiator monomers may be directly grafted to the surfaces of the base substrate upon exposure to e-beam irradiation. Those unreacted, ungrafted photoinitiator monomers will be incorporated into the growing polymer chain on exposure to UV radiation, thereby indirectly grafting the monomers to the porous base substrate. It will be further understood where multiple imbibing steps are used, one of more of the imbibing solutions may contain no photoinitiator monomers.

A variety of photoinitiator grafting monomers can be made by reaction of: 1) an acryloyl monomer comprising a first reactive functional group with 2) a compound that comprises a radiation-sensitive group (photoinitiator group) and second reactive functional group, the two functional groups being co-reactive with each other. Preferred co-reactive compounds are ethylenically unsaturated aliphatic, cycloaliphatic, and aromatic compounds having up to 36 carbon atoms, optionally one or more oxygen and/or nitrogen atoms, and at least one reactive functional group. When the first and second functional groups react, they form a covalent bond and link the co-reactive compounds.

Examples of useful reactive functional groups include hydroxyl, amino, oxazolinyl, oxazolonyl, acetyl, acetonyl, carboxyl, isocyanato, epoxy, aziridinyl, acyl halide, and cyclic anhydride groups. Where the first reactive functional group is an isocyanato functional group, the second, co-reactive functional group preferably comprises a amino, carboxyl, or hydroxyl group. Where first reactive functional group comprises a hydroxyl group, the second, co-reactive functional group preferably comprises a carboxyl, isocyanato, epoxy, anhydride, acyl halide, or oxazolinyl group. Where the first reactive functional group comprises a carboxyl group, the second co-reactive functional group preferably comprises a hydroxyl, amino, epoxy, vinyloxy, or oxazolinyl group.

Representative examples of acrylate compounds having a reactive functional group include hydroxyalkyl acrylates such as 2-hydroxyethyl acrylate and 2-(2-hydroxyethoxy) ethyl acrylate; aminoalkyl acrylates such as 3-aminopropyl acrylate; oxazolonyl compounds such as 2-ethenyl-1,3-oxazolin-5-one and 2-propenyl-4,4-dimethyl-1,3-oxazolin-5-one; carboxy-substituted compounds such as acrylic acid and 4-carboxybenzyl acrylate; isocyanato-substituted compounds such as isocyanatoethyl acrylate and 4-isocyanatocyclohexyl acrylate; epoxy-substituted compounds such as glycidyl acrylate; aziridinyl-substituted compounds such as N-acryloylaziridine; and acryloyl halides.

Representative examples of co-reactive compounds include functional group-substituted compounds such as 1-(4-hydroxyphenyl)-2,2-dimethoxyethanone, 1-[4-(2-hydroxyethyl)phenyl]-2,2-dimethoxyethanone, (4-isocyanatophenyl)-2,2-dimethoxy-2-phenylethanone, 1-{4-[2 (2,3-epoxypropoxy)phenyl]}-2,2-dimethyl-2-hydroxyethanone, 1-[4-(2-aminoethoxy)phenyl]-2,2-dimethoxyethanone, and 1-[4-(carbomethoxy)phenyl]-2,2-dimethoxyethanone.

It will be understood that all or a portion of the acrylate groups of the photoinitiator monomer may be directly grafted to the surface of the base substrate on irradiation. Those ungrafted, free acryloyl groups may be subsequently indirectly grafted to the substrate by incorporation into the polymer chain on UV initiated polymerization.

The second grafting "b)" ligand monomers comprise an acryloyl group and a ligand group having affinity for neutral or negatively charged biological materials. The ligand monomers are of the general formula, previously described:

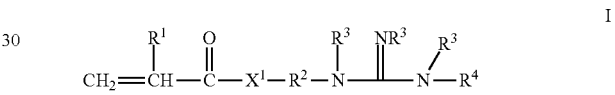

I wherein
$R^1$ is H or $C_1$-$C_4$ alkyl;
$R^2$ is a divalent alkylene, preferably having 1 to 2.0 carbon atoms and optionally containing an ester, amide, urethane or urea linking group;
each $R^3$ is independently H or $C_1$-$C_4$ alkyl;
$R^4$ is H, $C_1$-$C_4$ alkyl or —$N(R^3)_2$; and $X^1$ is —O— or —$NR^3$—.

Such ligand monomer may be made by condensation of an (meth)acryloyl compound, typically a (meth)acryloyl halide with a compound of the formula:

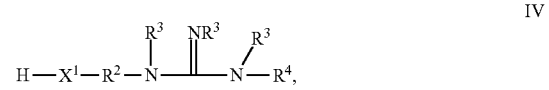

IV where $X^1$, and $R^2$ to $R^4$ are as previously defined.

In certain preferred embodiments, the ligand monomers are of the general formula:

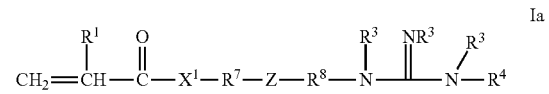

Ia where
$R^1$ is H or $C_1$-$C_4$ alkyl,
each $R^3$ is independently H or $C_1$-$C_4$ alkyl,
$R^4$ is H, $C_1$-$C_4$ alkyl or —$N(R^3)_2$,
$X^1$ is —O— or —$NR^3$—, where $R^3$ is H or $C_1$-$C_4$ alkyl,
$R^7$ and $R^8$ are each independently C to $C_1$ to $C_{10}$ alkylene; and Z is an ester, amide, urea, or urethane group. Preferably the sum of carbon atoms in $R^7$ and $R^8$ is 2 to 10.

In a manner similar to that described for the photoinitiator monomers of Formula XII, the ligand monomers of Formula Ia can be made by reaction of: 1) an acryloyl monomer comprising a first reactive functional group with 2) a compound that comprises a ligand group and second reactive functional group (such as those of Formula IV), the two functional groups being co-reactive with each other. When the first and second functional groups react, they form a covalent bond and link the co-reactive compounds by the indicated "Z" group. In some embodiments, ligand monomers of Formula Ia may be prepared by the reaction of an alkenyl oxazolinone with a compound of Formula IV.

It will be understood that all or a portion of the acryloyl groups of the ligand monomer I or Ia may be directly grafted to the surface(s) of the substrate on exposure of ionizing radiation if incorporated into the first imbibing step, or may be subsequently indirectly grafted to the substrate by incorporation into the polymer chain on UV initiated polymerization.

If directly grafted, the surface(s) of the base substrate may comprise ligand groups attached thereto of the formula:

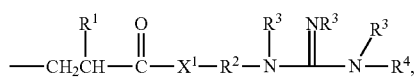

V where $X^1$, and $R^1$ to $R^4$ are as previously defined.

If indirectly grafted, the ligand monomer will be grafted via the residue of the photoinitiator and the base substrate will have ligand groups attached thereto of the formula:

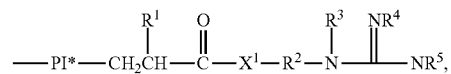

VI wherein
$R^1$, $R^2$, $R^3$, $R^4$, $R^5$ and $X^1$ as previously defined; and
PI* is the residue of a photoinitiator grafted to the substrate surface. For example a grafting photoinitiator monomer such as 2-propenoylaminoethanoic acid; 2-(4-(2-hydroxy-2 methylpropanoyl)phenoxy)ethyl ester may be grafted to a substrate surface using ionizing radiation such as e-beam energy. In the presence of UV, the photoinitiator undergoes alpha cleavage to two radicals. In the presence of the ligand monomer, or other monomers, the radical may add to the ethylenically unsaturated group (such as the depicted acryloyl group) to indirectly graft the ligand monomer to the substrate surface via the residue of the photoinitiator as shown in formula VI and illustrated in Scheme I below. It will be further understood that the radical addition product of the ligand monomer may further copolymerize with additional ligand monomers and the other optional monomers to produce a grafted polymer having ligand groups pendent therefrom.

Scheme I

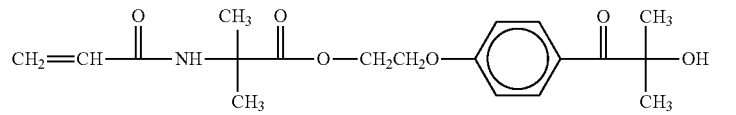

↓ grafting

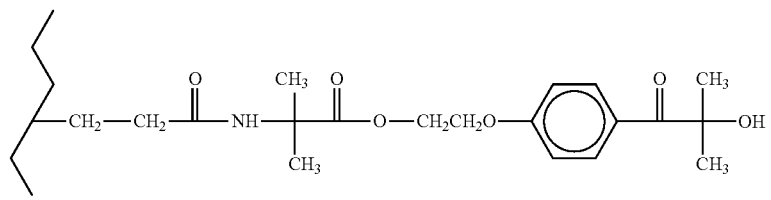

↓ uv

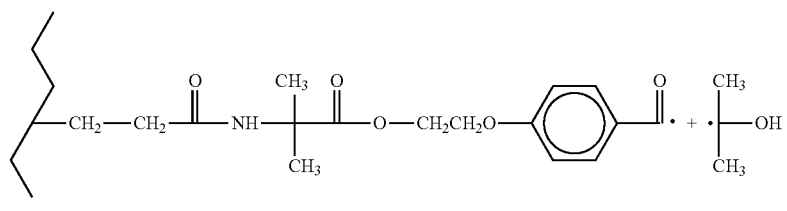

↓ addition

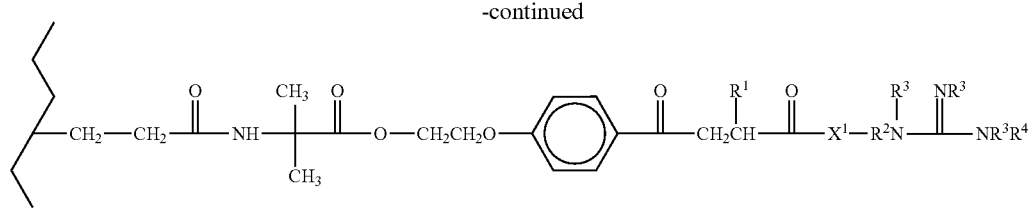

-continued

It will be further understood that the grafting process will yield a radical species, having a radical on the carbon alpha to the carbonyl of the ligand monomer or Formula I, that may further polymerize with one of more additional ligand "b" monomers, one of more photoinitiator "a" monomers, one or more "c)" monomers and or one of more "d)" monomers, resulting in a grafted polymers having these groups pendent from the polymer chain as simply illustrated below. The formation of grafted polymer chains significantly increases the density of the desired ligand groups, and the efficiency of binding.

Substrate-$(M^{PI})$-$(M^b)_x$-$(M^c)_y$-$(M^d)_z$

In the formula, the -$(M^{PI})$- represent the residue of the grafted photoinitiator monomer (as illustrated in Scheme I, the -$(M^b)_x$, represents the polymerized ligand monomer, having "x" polymerized monomer units, where x is at least one and preferably at least two, -$(M^c)_y$ represents the polymerized monomer "c)", having y polymerized monomer units, where y may be zero and is preferably at least 1 and -$(M^d)_z$ represents the polymerized monomer "d)" having z polymerized monomer units, where z may be zero and is preferably at least 1. The polymer may be random or block, and the "c)" monomer, having two polymerizable groups may provide crosslink between polymer chains. The polymer may be directly grafted via the residue of the photoinitiator, as shown in Scheme I, or may be directly grafted via the ligand "b)" monomers as shown in Formula V, the "c)" monomers or the "d)" monomers, as described herein. The polymer may further comprise polymerized photoinitiator monomer units from unreacted, ungrafted photoinitiator monomers.

The third grafting "c)" monomers comprises (a) one or more acryloyl groups for grafting and (b) one or more second, ethylenically unsaturated, free-radically polymerizable groups for subsequent crosslinking. The second ethylenically unsaturated group may be an acrylate or a non-acrylate; i.e. other ethylenically unsaturated groups having reduced reactivity relative to the acrylate group during the e-beam grafting step. Preferably the second ethylenically unsaturated group is a non-acrylate group and is left largely free and unreacted during the grafting step for subsequent UV crosslinking. Useful second, non-acrylate ethylenically unsaturated groups include methacrylates, (meth)acrylamides, vinyl groups, vinyloxy, acetylenic groups, allyl and allyloxy groups.

Useful third grafting monomers "c)" may have the generalized structure:

$[CH_2=CH-C(O)-X^1]_a-R^{10}-Q-Z_b$,  VII where Z is an acryloyl or non-acryloyl, ethylenically unsaturated polymerizable group,
$X^1$ is —O— or —NR$^3$, where R$^3$ is H or $C_1$-$C_4$ alkyl,
Q is a divalent linking group selected from a covalent bond "—", —O—, —NR$^1$—, —CO$_2$— and —CONR$^1$—, where R$^1$ is H or $C_1$-$C_4$ alkyl; and
R$^{10}$ is an alkylene group of valence a+b, preferably having 1 to 20 carbon atoms and optionally containing, one or more catenary oxygen atoms and/or one or more hydroxyl groups; and a and b are each at least one. Preferably the Z group is a non-acryloyl of reduced reactivity that is indirectly grafted into the polymer chain during UV initiated polymerization.

In certain embodiments, R$^{10}$ is a poly(alkylene oxide group) to provide hydrophilicity to the functionalized substrate, and is of the formula:

Z-Q-(CH(R$^1$)—CH$_2$—O)$_n$—C(O)—CH=CH$_2$,  VIII wherein Z is an acryloyl or non-acryloyl, polymerizable ethylenically unsaturated group,
R$^1$ is a H or a $C_1$ to $C_4$ alkyl group, and n is from 2 to 100, preferably 5 to 20, and Q is a divalent linking group selected front a covalent bond "—", —O—, —NR—$^1$—, —CO$_2$— and —CONR$^1$—, where R$^1$ is H or $C_1$-$C_4$ alkyl. Preferably the Z group is a non-acrylate of reduced reactivity that is indirectly grafted into the polymer chain during UV initiated polymerization.

In one embodiment, the poly(alkylene oxide) group (depicted as —(CH(R$^1$)—CH$_2$—O)$_n$—) is a poly(ethylene oxide) (co)polymer. In another embodiment, the poly(alkylene oxide) group is a poly(ethylene oxide-co-propylene oxide) copolymer. Such copolymers may be block copolymers, random copolymers, or gradient copolymers.

Suitable monomers having a first acryloyl group for grafting and a second ethylenically unsaturated group for subsequent UV polymerization include, but are not limited to, polyalkylene glycol acrylate methacrylate including those derived from polyethylene glycol and polypropylene glycol acrylated monomers.

In another embodiment, the third "c)" monomer is a partially acrylated polyol, having at least one acrylate groups and at least one other ethylenically unsaturated polymerizable group, which is preferably not a acrylate group and may be selected from methacrylates, (meth)acrylamides, vinyl groups, vinyloxy, acetylenic groups, ally and allyloxy groups. Such partially acrylated polyols may have one or more free hydroxyl groups.

Polyols useful in the present invention include aliphatic, cycloaliphatic, or alkanol-substituted arene polyols, or mixtures thereof having from about 2 to about 18 carbon atoms and two to five, preferably two to four hydroxyl groups.

Examples of useful polyols include 1,2-ethanediol, 1,2-propanediol, 1,3-propanediol, 1,4-butanediol, 1,3-butanediol, 2-methyl-1,3-propanediol, 2,2-dimethyl-1,3-propanediol, 2-ethyl-1,6-hexanediol, 1,5-pentanediol, 1,6-hexanediol, 1,8-octanediol, neopentyl glycol, glycerol, trimethylolpropane, 1,2,6-hexanetriol, trimethylolethane, pentaerythritol, quinitol, mannitol, sorbitol, diethlene glycol, trimethylene glycol, tetraethylene glycol, 2-ethyl-2-(hydroxymethyl)-1,3-propanediol, 2-ethyl-1,3-pentanediol, 1,4-cyclohexanedimethanol, 1,4-benzenedimethanol, and polyalkoxylated bisphenol A derivatives. Most preferably, "c)" monomers are those monoacrylates of glycerol having a free hydroxyl group and a methacrylate group such as 3-(acryloxy)-2-hydroxypropylmethacrylate).

In some preferred embodiments, the ethylenically unsaturated, free-radically polymerizable groups of the ligand "b)" and ethylenically unsaturated "c)" monomers and hydrophilic "d)" monomers are chosen to be efficiently copolymerizable with each other. That is, it is preferred that each of the "b)", "c)" and "d)" monomers have the same polymerizable groups.

In one exemplary embodiment, the grafted species results from the reaction of a polyethylene glycol acrylate monomer of Formulas VII or VIII with the base substrate upon exposure to an ionizing radiation preferably e-beam or gamma radiation. These grafting monomers can be used to change a hydrophobic porous base substrate into a hydrophilic functionalized substrate due to the presence of the poly(alkylene oxide) group. The resulting hydrophilic substrate can have a number of desired properties such as instant wettability. For some hydrophobic substrates such as those prepared from poly(vinylidene fluoride) (PVDF) it is preferred to imbibe and graft first with a hydrophilic "c)" monomer of Formulas VII or VIII prior to imbibing and grafting with the photoinitiator a) monomer and ligand b) monomer to render the substrate hydrophilic prior to ligand functionalization.

The optional fourth hydrophilic monomer "d)", comprises at least one acryloyl or other non-acryloyl group of reduced reactivity, and a hydrophilic group, including poly(oxyalkylene) and ionic groups, for providing hydrophilicity to the substrate, or for providing greater selectivity to the substrate when binding viruses. If the optional fourth monomer contains an acryloyl group, it may be directly grafted to the surface(s) of the base substrate. If it contains a non-acryloyl, ethylenically unsaturated group it may remain largely unreacted during the grafting step, and will be incorporated during the UV polymerization step. It will be understood that all or a portion of the acryloyl groups may be directly grafted to the porous substrate, and a portion may be unreacted, but will be indirectly grafted into the polymer upon UV initiated irradiation. Conversely, a portion of other ethylenically unsaturated groups of reduced reactivity may be directly grafted, but such groups generally remain largely unreacted during the grafting step and are indirectly grafted into the polymer upon UV initiated irradiation.

The hydrophilic ionic groups may be neutral, have a positive charge, a negative charge, or a combination thereof. With some suitable ionic monomers, the ionic group can be neutral or charged depending on the pH conditions. This class of monomers is typically used to impart a desired hydrophilicity to the porous base substrate in addition to the c) monomer. In applications for viral capture, the addition of a grafting ionic monomer having a positive charge at the selected pH may allow selective binding of viruses while repelling positively charged biological materials such as antibodies.

In some preferred embodiments, the third monomer may have an acrylate group, or other ethylenically unsaturated groups of reduced reactivity, and a poly(alkylene oxide) group; e.g. monoacrylated poly(alkylene oxide compounds, where the terminus is a hydroxy group, or an alkyl ether group.

In some embodiments the ionic monomers having a negative charge include meth)acryloylsulfonic acids of Formula IX or salts thereof.

wherein, Y is a straight or branched alkylene (e.g., an alkylenes having 1 to 10 carbon atoms, 1 to 6 carbon atoms, or 1 to 4 carbon atoms) and L is —O— or —$NR^3$—, where $R^3$ is H or $C_1$-$C_4$ alkyl-;. Exemplary ionic monomers according to Formula IX include, but are not limited to, N-acrylamidomethanesulfonic acid, 2-acrylamidoethanesulfonic acid, 2-acrylamido-2-methyl-1-propanesulfonic acid, and 2-methacrylamido-2-methyl-1-propanesulfonic acid. Salts of these acidic monomers can also be used. Counter ions for the salts can be, for example, ammonium ions, potassium ions, lithium ions, or sodium ions. It will be understood with respect to Formula IX that the grafting acryloyl group may be replaced by another ethylenically unsaturated group of reduced reactivity for subsequent incorporation (indirect grafting) during UV initiated polymerization.

Other suitable ionic grafting monomers having a negative charge (at a selected pH) include sulfonic acids such as vinylsulfonic acid and 4-styrenesulfonic acid; (meth)acrylamidophosphonic acids such as (meth)acrylamidoalkylphosphonic acids (e.g., 2-(meth)acrylamidoethylphosphonic acid and 3-meth)acrylamidopropylphosphonic acid; acrylic acid and methacrylic acid; and carboxyalkyl(meth)acrylates such as 2-carboxyethyl(meth)acrylate, and 3-carboxypropyl(meth)acrylate. Still other suitable acidic monomers include (meth)acryloylamino acids, such as those described in U.S. Pat. No. 4,157,418 (Heilmann). Exemplary (meth)acryloylamino acids include, but are not limited to N-acryloylglycine, N-acryloylaspartic acid, N-acryloyl-β-alanine, and 2-acrylamidoglycolic acid. Salts of any of these acidic monomers can also be used.

Some exemplary ionic grafting monomers that are capable of providing a positive charge (at a selected pH) are amino (meth)acrylates or amino(meth)acrylamides of Formula X or quaternary ammonium salts thereof. The counterions of the quaternary ammonium salts are often halides, sulfates, phosphates, nitrates, and the like.

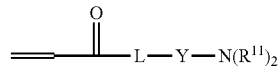

where L is —O— or —$NR^3$—, where $R^3$ is H or $C_1$-$C_4$ alkyl-; and Y is an alkylene (e.g., an alkylene having 1 to 10 carbon atoms, 1 to 6, or 1 to 4 carbon atoms). Each $R^{11}$ is independently hydrogen, alkyl, hydroxyalkyl (i.e., an alkyl substituted with a hydroxy), or aminoalkyl (i.e., an alkyl substituted, with an amino). Alternatively, the two $R^{11}$ groups taken together with the nitrogen atom to which they are attached can form a heterocyclic group that is aromatic, partially unsaturated (i.e., unsaturated but not aromatic), or saturated, wherein the heterocyclic group can optionally be fused to a second ring that is aromatic (e.g., benzene), partially unsaturated (e.g., cyclohexene), or saturated (e.g., cyclohexane).

It will be understood with respect to Formulas IX and X that the grafting acryloyl group may be replaced by another ethylenically unsaturated group of reduced reactivity, such as methacrylate, methacrylamide, vinyl, vinyloxy, ally, alloxy, and acetylenyl for subsequent incorporation (indirect grafting) during UV initiated polymerization.

In some embodiments of Formula X, both $R^{11}$ groups are hydrogen. In other embodiments, one $R^{11}$ group is hydrogen and the other is an alkyl having 1 to 10, 1 to 6, or 1 to 4 carbon atoms. In still other embodiments, at least one of $R^{11}$ groups is a hydroxy alkyl or an amino alkyl that have 1 to 10, 1 to 6, or 1 to 4 carbon atoms with the hydroxy or amino group being positioned on any of the carbon atoms of the alkyl group. In yet other embodiments, the $R^{11}$ groups combine with the nitrogen atom to which they are attached to form a heterocyclic group. The heterocyclic group includes at least one nitrogen atom and can contain other heteroatoms such as oxygen or sulfur. Exemplary heterocyclic groups include, but are not limited to imidazolyl. The heterocyclic group can be fused to an additional ring such as a benzene, cyclohexene, or cyclohexane. Exemplary heterocyclic groups fused to an additional ring include, but are not limited to, benzoimidazolyl.

Exemplary amino acrylates (i.e., L in Formula X is —O—) include N,N-dialkylaminoalkyl acrylates such as, for example, N,N-dimethylaminoethylacrylate, N,N-dimethylaminoethylacrylate, N,N-diethylaminoethyl acylate, N,N-diethylaminoethylacrylate, N,N-dimethylaminopropylacrylate, N,N-dimethylaminopropylacrylate, N-tert-butylaminopropylmethacrylate, N-tert-butylaminopropylacrylate and the like.

Exemplary amino(meth)acrylamides, (i.e., L in Formula X is —$NR^3$—) include, for example, N-(3-aminopropyl)methacrylamide, N-(3-aminopropyl)acrylamide, N-[3-(dimethylamino)propyl]methacrylamide, N-(2-imidazolylpropyl)methacrylamide, N-(3-imidazolylpropyl)acrylamide, N-(2-imidazolylethyl)methacrylamide, N-(1,1-dimethyl-3-imidazolylpropyl)methacrylamide, N-(1,1-dimethyl-3-imidazoylpropyl)acrylamide, N-(3-benzoimidazolylpropyl)acrylamide, and N-(3-benzoimidazolylpropyl)methacrylamide.

Exemplary quaternary salts of the ionic monomers of Formula X include, but are not limited to, (meth)acrylamidoalkyltrimethylammonium salts (e.g., 3-methacrylamidopropyltrimethylammonium chloride and 3-acrylamidopropyltrimethylammonium chloride) and (meth)acryloxyalkyltrimethylammonium salts (e.g., 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate).

Other monomers that can provide positively charged groups (at a selected pH) to the base substrate include the dialkylaminoalkylamine adducts of alkenylazlactones (e.g., 2-(diethylamino)ethylamine, (2-aminoethyl)trimethylammonium chloride, and 3-(dimethylamino)propylamine adducts of vinyldimethylazlactone) and diallylamine monomers (e.g., diallylammonium chloride and diallyldimethylammonium chloride). Others include the alkenylazlactones adducts of polyetheramines (such as the monoamine, diamine and triamines based on the polyetheramine structure). One example of these compounds is the Jeffamine®, series, from Huntsman, The Woodlands, Tex., USA. Other examples include the quaternary salt of dimethylaminoethyl methacrylate.

A fourth, neutral d) monomer, that may be incorporated by direct grafting or during subsequent UV polymerization (indirect grafting) are poly(alkylene oxide) monomers having a (meth)acryloyl or non-acryloyl ethylenically unsaturated group and a non-polymerizable terminus. Such monomers may be of the formula:

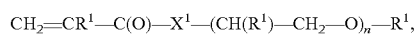   XI wherein each $R^1$ is independently H or $C_1$-$C_4$ alkyl, $X^1$ is —O— or —$NR^3$—, where $R^3$ is H or $C_1$-$C_4$ alkyl.

As described in further detail below, functionalized substrates may be prepared using above-described d) monomers to provide hydrophilicity or ionic character to the surface of a base substrate. When two or more of the above-described monomers are used to alter the surface properties of a base substrate, the monomers may be grafted onto the base substrate in a single reaction step (i.e., the two or more grafting monomers are all present upon exposure to ionizing radiation) or in sequential reaction steps (i.e., a first grafting photoinitiator monomer "a)", is present upon a first exposure to ionizing radiation and a second grafting monomer "b) and/or c)" is present upon a second exposure to the ionizing radiation). Similarly, all of such monomers a), b), c) and d) may be present during a first grafting step and directly grafted, or indirectly grafted by incorporation during the subsequent UV initiated polymerization. Alternatively, all or a portion of such monomers may be imbibed in a first step, or in subsequent imbibing steps. Alternatively, hydrophobic substrates may be rendered hydrophilic by first imbibing and grafting with a hydrophilic monomer, such as represented by Formulas VIII or XI and then subsequently imbibing and directly grafting with the photoinitiator a) monomers, and imbibing and directly or indirectly grafting with the other b), c) and d) monomers.

The above-described ligand functionalized substrates may be prepared using a combination of process steps. The method comprises:

1) providing a base substrate, preferably a porous base substrate having interstitial and outer surfaces;

2) coating the base substrate (preferably imbibing the porous substrate) with a solution comprising (a) at least one grafting monomer having an acryloyl group and a photoinitiator group of Formula XII; (b) one or more ligand b) monomers of Formulas I or Ia, (c) optionally one or more c) monomers having at least one acryloyl group and at least one additional ethylenically unsaturated, free-radically polymerizable group of Formulas VII or VIII; and (d) optionally one or more hydrophilic d) monomers of Formulas IX, X or XI;

3) exposing the coated substrate (or imbibed porous base substrate) to ionizing radiation so as to form a first functionalized substrate comprising grafted photoinitiator group attached to the surface(s) of the base substrate, and 4) exposing the base substrate comprising grafted photoinitiator groups to UV radiation to polymerize the remaining ethylenically unsaturated, free-radically polymerizable groups In a particularly preferred embodiment, the method comprises:

1) providing a base substrate, preferably a porous base substrate having interstitial and outer surfaces;

2) coating the base substrate (preferably imbibing the porous substrate) with a first solution comprising (a) at least one grafting monomer having an acryloyl group and a photoinitiator group of Formula XII; (b) optionally one or more ligand monomers of Formulas I or Ia, (c) optionally one or more monomers baying at least one acryloyl group and at least one additional ethylenically unsaturated, free-radically polymerizable group of Formulas VII or VIII; and (d) optionally one or more hydrophilic monomers of Formulas IX, X or XI;

3) exposing the coated substrate (or imbibed porous base substrate) to ionizing radiation, preferably e-beam or gamma radiation, so as to form a first functionalized substrate comprising a base substrate having grafted photoinitiator group attached to the surface(s) thereof;

4) coating the base substrate (preferably imbibing the porous substrate) having grafted photoinitiator groups with a second solution comprising (b) one or more of said ligand monomers, (c) optionally one or more monomers having at least one acryloyl group and at least one additional ethylenically unsaturated, free-radically polymerizable group; and (d) optionally one or more hydrophilic monomers;

5) exposing the base substrate comprising grafted photoinitiator groups to UV radiation to polymerize the remaining ethylenically unsaturated, free-radically polymerizable groups.

The methods of the present disclosure involve the irradiation of porous or non-porous substrate surfaces with ionizing radiation to prepare free radical reaction sites on such surfaces upon which the monomers are grafted. "Ionizing radiation" means radiation of a sufficient dosage and energy to cause the formation of free radical reaction sites on the surface(s) of the base substrate. Ionizing radiation may include beta, gamma, electron-beam, x-ray and other electromagnetic radiation. In some instances, corona radiation can be sufficiently high energy radiation. The radiation is sufficiently high energy, that when absorbed by the surfaces of the base substrate, sufficient energy is transferred to that support to result in the cleavage of chemical bonds in that support and the resultant formation of a free radical site on the support.

High energy radiation dosages are measured in megarads (Mrad) or kilograys (kGy), which is ¹/₁₀ of a mRad. Doses can be administered in a single dose of the desired level or in multiple doses which accumulate to the desired level. Dosages can range cumulatively from about 1 kGys to about 100 kGys. Preferably, the cumulative dosage exceeds 30 kGys (3 Mrads) for substrate resistant to radiation damage.

Electron beam and gamma radiation are preferred for this method of grafting due to the ready-availability of commercial sources. Electron beam generators are commercially available from a variety of sources, including the ESI "ELECTROCURE" EB SYSTEM from Energy Sciences, Inc. (Wilmington, Mass.), and the BROADBEAM PB PROCESSOR from PCT Engineered Systems, LLC (Davenport, Iowa). Sources of gamma irradiation are commercially available from MDS Nordion using a cobalt-60 high-energy source. For any given piece of equipment and irradiation sample location, the dosage delivered can be measured in accordance with ASTM E-1275 entitled "Practice for Use of a Radiochromic Film Dosimetry System." By altering extractor grid voltage, beam diameter and/or distance to the source, various dose rates can be obtained.

The base substrate may be nonporous or porous. Some of the porous base substrates used in this embodiment can be porous, microporous, nonwoven, or a combination thereof.

One exemplary method for making functionalized substrates is depicted in FIG. 1. As shown in FIG. 1, exemplary method 10 comprises the following steps: an imbibing step 100, a sandwiching step 200, an irradiation step 300, a UV initiated polymerization step 400, a peeling step 500, a wash/rinse step 600, a drying step 700, and a take-up step 800. Each of these exemplary steps is described in further detail below.

Methods of making functionalized substrates of the present invention may comprise one or more of the following steps.
Imbibing Step As shown in FIG. 1, a roll 11 comprising a base substrate, preferably a porous base substrate 12 may be unwound so that porous base substrate 12 enters into imbibing step 100. In imbibing step 100, base substrate 12 is brought into contact or into proximity with applicator 14 that is connected to a reservoir of solution 13 containing one or more grafting monomers. Rollers 15 and 16 amide base substrate 12 past applicator 14 so that base substrate 12 is exposed to solution 13 for a desired amount of time. Typically, the exposure time of the porous base substrate 12 to solution 13 is up to about 1.0 minutes, more typically, less than about 15 seconds. Base substrate 12 usually proceeds through imbibing step 100 and to irradiation step 300 in less than 1 minute. In some imbibing steps, the base substrate 12 is saturated with the solution 13.

As discussed above, solution 13 may comprise one or more grafting monomers suitable for grafting onto surfaces or the base substrate, preferably the interstitial and outer surfaces of porous base substrate 12. Any of the exemplary grafting monomers described above can be included in solution 13. In addition to grafting monomers, solution 13 can contain other materials such as, for example, one or more other non-grafting monomers for UV curing, and solvents. The concentration of each grafting monomer in solution 13 may vary depending on a number of factors including, but not limited to, the grafting monomer or monomers in solution 13, the extent of grafting desired, the reactivity of the grafting monomer(s), and the solvent used. Typically, the concentration of each monomer in solution 13 ranges from about 1 wt % to about 100 wt %, desirably, from about 5 wt % to about 30 wt %, and more desirably from about 10 wt % to about 20 wt % based on a total weight of solution 13.

Once base substrate 12 has been imbibed in solution 13 for a desired period of time, the base substrate 12 is directed toward sandwiching step 200 via guide roller 17. Guide roller 17 may be used to meter excess solution 13 from the imbibed base substrate 12 if so desired. Alternately, rollers not shown) could be used to squeeze air bubbles and excess solution 13 from the imbibed base substrate 12. Typically, base substrate 12 enters sandwiching step 200 in a substantially saturated condition (i.e., base substrate 12 contains a maximum amount of solution 13 or close to a maximum amount) wherein substantially all the surface(s), preferably all the interstitial and outer surfaces of porous base substrate 12 are coated with solution 13.

It should be noted that imbibing step 100 is only one possible method of introducing solution 13 into porous base substrate 12. Other suitable methods include, but are not limited to, a spray coating, flood coating, knife coating, Meyer bar coating, dip coating, and gravure coating.
Sandwiching Step In sandwiching step 200, imbibed base substrate 12 is sandwiched (i.e., positioned) between a removable carrier layer 22 and a removable cover layer 19 to form multilayer sandwich structure 24. As shown in exemplary method 10, removable cover layer 19 may be unwound from roll 18 and brought into contact with an outer surface of imbibed base substrate 12 via roller 20, while removable carrier layer 22 may be unwound from roll 21 and brought into contact with an opposite outer surface of imbibed base substrate 12 via roller 23. Rollers 20 and 23 form a gap that may be used to regulate the amount of imbibing solution 13 imparted to the porous substrate. The removable cover layers 19 and 22 serve to exclude oxygen from the subsequent radical processes and also to prevent draining of the imbibing solution 13.

Removable cover layer 19 and removable carrier layer 22 may comprise any inert sheet material that is capable of providing temporary protection to functionalized substrate 30 (i.e., grafted base substrate 12) from direct exposure to oxygen upon exiting chamber 25. Suitable inert sheet materials for forming removable cover layer 19 and removable carrier layer 22 include, but are not limited to, polyethylene terephthalate film material, other aromatic polymer film materials, and any other non-reactive polymer film material. In some embodiments, removable carrier layer 22 may be selected from materials that are transparent to UV radiation. Once assembled, multilayer sandwich structure 24 proceeds to irradiation step 300.

In irradiation step 300, multilayer sandwich structure 24 is exposed to a sufficient quantity of ionizing radiation (preferably e-beam or gamma radiation), so as to graft one or more monomers within solution 13 onto surfaces of base substrate 12 so as to form multilayer sandwich structure 27 comprising functionalized substrate 30 sandwiched between removable carrier layer 22 and removable cover layer 19. As shown in exemplary method 10, multilayer sandwich structure 24 proceeds through chamber 25, which contains at least one device 26 capable of providing a sufficient dose of radiation. A single device 26 is capable of providing a sufficient dose of radiation, although two or more devices 26 may be used especially for relatively thick porous base substrates 12. Typically, chamber 25 comprises an inert atmosphere such as nitrogen, carbon dioxide, helium, argon, etc. with at minimal amount of oxygen, which is known to inhibit free-radical polymerization. In embodiments wherein base substrate 12 is irradiated without removable cover layer 19, the amount of oxygen within chamber 25 can be more of a concern. When removable carrier layer 22 and removable cover layer 19 cover the porous base substrate 12, exposure to oxygen within chamber 25 is minimal.

The irradiation step 300 provides the further advantage of converting any dissolved oxygen to peroxy compounds, which would interfere with the subsequent UV initiated polymerization. Therefore the e-beam irradiation step 300 facilitates the subsequent UV initiation 400 by the removal of oxygen.

Although other sources of irradiation may be used, desirably device 26 comprises an electron beam source. Electron beams (e-beams) are generally produced by applying high voltage to tungsten wire filaments retained between a repeller plate and an extractor grid within a vacuum chamber maintained at about $10^{-6}$ Torr. The filaments are heated at high current to produce electrons. The electrons are guided and accelerated by the repeller plate and extractor grid towards a thin window of metal foil. The accelerated electrons, traveling at speeds in excess of $10^7$ meters/second (m/sec) and possessing about 100 to 300 kilo-electron volts (keV), pass out of the vacuum chamber through the foil window and penetrate whatever material is positioned immediately beyond the foil window.

The quantity of electrons generated is directly related to the current. As extractor grid voltage is increased, the acceleration or speed of electrons drawn from the tungsten wire filaments increase. E-beam processing can be extremely precise when under computer control, such that an exact dose and dose rate of electrons can be directed against multilayer sandwich structure 24.

The temperature within chamber 25 is desirably maintained at an ambient temperature by conventional means. Without intending to be limited to any particular mechanism, it is believed that the exposure of the imbibed porous base substrate to an electron beam results in free radical initiation on the substrate which can then react with monomers having a double bond such as monomers having an ethylenically unsaturated group.

The total dose received by multilayer sandwich structure 24 primarily affects the extent to which the grafting monomer is grafted onto the porous base substrate. In general, it is desirable and typical to convert at least 10 wt %, desirably 20 wt %, even more desirably greater than 50 wt % of the grafting monomers added during the imbibing step to directly grafted species. Further, it is desirable and typical to graft as much as about 5 wt %, desirably as much as about 10 wt %, more desirably as much as about 20 wt % (or as much as about 100 wt %) of one or more grafting monomers added during the imbibing step onto base substrate 12, based on a total weight of porous base substrate 12. Dose is dependent upon a number of processing parameters, including voltage, speed and beam current. Dose can be conveniently regulated by controlling line speed (i.e., the speed with which multilayer sandwich structure 24 so passes under device 26), and the current supplied to the extractor grid. A target dose e.g., <10 kGy) can be conveniently calculated by multiplying an experimentally measured coefficient (a machine constant) by the beam current and dividing by the web speed to determine the exposure. The machine constant varies as a function of beam voltage.

While the controlled amount of electron beam radiation exposure is dependent upon the residence time, as a general matter, the monomers imbibed on the base substrate 12 that is part of multilayer sandwich structure 24 will generally be significantly grafted upon receiving a controlled amount of dosage ranging from a minimum dosage of about 1 kilograys (kGy) to a maximum dosage of less than about 100 kGy, depending on the particular polymer. For radiation sensitive polymers such as propylene polymers the amount typically ranges from a minimum dosage of about 1 kilograys (kGy) to a maximum dosage of less than about 10 kGy. Typically, the total controlled amount of dosage ranges front less than about 9 kGy to about 7 kGy for propylene polymers to avoid degradation. Less radiation sensitive polymers such as nylons or PVDF may be subjected to higher dosages, typically 10 to 70 kGy.

While low dose rates and longer residence times are preferred for radiation grafting, practical operation may necessitate speeds that farce higher dose rates and shorter residence. Exclusion of oxygen in a multilayer sandwich allows free radical chemistry to continue after ionizing radiation exposure for duration sufficient to in the grafting yield. Although not depicted, in some embodiments the method may comprise additional imbibing and grafting steps, followed by a UV curing step.

UV Curing Step

In UV irradiation step 400, multilayer sandwich structure 24 is exposed to a sufficient quantity of ultraviolet radiation so as to initiate free radical polymerization between the grafted photoinitiator groups and any free, unreacted acryloyl groups and or other ethylenically unsaturated groups. The polymerization of the unreacted ethylenically unsaturated groups onto the grafted surfaces of base substrate 12 forms multilayer sandwich structure 27 comprising functionalized substrate 30 sandwiched between removable carrier layer 22 and removable cover layer 19. As shown in exemplary method 10, multilayer or sandwich structure 24 proceeds through chamber 40, which contains at least one device 41 capable of providing a sufficient dose of UV radiation. A single device 41 is capable of providing a sufficient dose of radiation, although two or more devices 41 may be used especially for relatively thick base substrates 12 or to double the lamp output. Upon UV irradiation, essentially all remaining acryloyl and non-acryloyl groups are incorporated into a polymer coating on the surfaces of the base substrate 12.

Typically, chamber 40 comprises an inert atmosphere such as nitrogen, carbon dioxide, helium, argon, etc. with a minimal amount of oxygen, which is known to inhibit free-radical polymerization. In embodiments wherein base substrate 12 is irradiated without removable cover layer 19, the amount of oxygen within chamber 25 can be more of a concern. When removable carrier layer 22 and removable cover layer 19 cover the base substrate 12, exposure to oxygen within chamber 25 is minimal.

UV light sources can be relatively low light intensity sources such as blacklights which provide generally 1.0 mW/cm$^2$ or less (as measured in accordance with procedures approved by the United States National Institute of Standards and Technology as, for example, with a UVIMAP™ UM 365 L-S radiometer manufactured by Electronic Instrumentation & Technology, Inc, in Sterling, Va.) over a wavelength range of 280 to 400 nanometers, or relatively high light intensity sources such as medium pressure mercury lamps which provide intensities generally greater than 10 mW/cm$^2$, preferably between 15 and 450 mW/cm$^2$. Where UV radiation is used to fully or partially polymerize the composition, moderate intensities and longer exposure times are preferred. For example, an intensity of about 10 to 50 mW/cm$^2$ and an exposure time of about 1 to 5 seconds may be used successfully. A preferred UV source is the Quant 48™ UV Curing System from Quantum Technologies, Irvine, Calif.

Peeling Step

Upon exiting chamber 25, multilayer sandwich structure 27 proceeds toward peeling step 500. In peeling step 500, multilayer sandwich structure 27 is disassembled by separating removable carrier layer 22 and removable cover layer 19 from functionalized substrate 30. As shown in exemplary method 10, removable cover layer 19 is separated from an outer surface of functionalized substrate 30 and taken-up as roll 28, while removable carrier layer 22 is separated from an opposite outer surface of functionalized substrate 30 and taken-up as roll 29.

In one desired embodiment, after exposure to an electron beam, UV curing, and exiting chamber 40, removable carrier layer 22 and removable cover layer 19 are allowed to remain on functionalized substrate 30 for a period of time prior to peeling step 400 so as to provide prolonged protection of functionalized substrate 30 from exposure to oxygen. Desirably, removable carrier layer 22 and removable cover layer 19 remain on functionalized substrate 30 for at least 15 seconds, more desirably, for about 30 to about 60 seconds after exiting chamber 25. However, there is no upper time limit that will reduce grafting quality and multilayer sandwich structure 27 can remain intact for an extended time period as would be the case if batch processing rolls of multilayer sandwich structure 27 are prepared. Once multilayer sandwich structure 27 is disassembled, functionalized substrate 30 can proceed to an optional washing/rinsing step 600.

In optional washing/rinsing step 600, functionalized substrate 30 is washed or rinsed one or more times in rinse chamber 31 to remove any unreacted monomers, solvent or other reaction by-products from functionalized substrate 30. Typically, functionalized substrate 30 is washed or rinsed up to three times using a water rinse, an alcohol rinse, a combination of water and alcohol rinses, and/or a solvent rinse (e.g., acetone, MEK, etc). When an alcohol rinse is used, the rinse may include one or more alcohols including, but not limited to, isopropanol, methanol, ethanol, or any other alcohol that is practical to use and an effective solvent for any residual monomer. In each rinse step, functionalized substrate 30 may pass through a rinse bath or a rinse spray.

In optional drying step 700, functionalized substrate 30 is dried to remove any rinse solution from functionalized substrate 30. Typically, functionalized substrate 30 is dried in oven 32 having a relatively low oven temperature for a desired period of time (referred to herein as "oven dwell time"). Oven temperatures typically range from about 60° C. to about 120° C., while oven dwell time typically range from about 120 to about 600 seconds. Any conventional oven may be used in optional drying step 700 of the present invention. Suitable ovens include, but are not limited to, a convection oven.

It should also be noted that in other embodiments drying step 700 can proceed before washing/rinsing step 600 eliminating volatile components before extraction of non-grafted residue.

Following optional drying step 700, dried functionalized substrate 30 can be taken up in roll form as roll 33 in step 800. Functionalized substrate 30 may be stored for future use in roll form, used immediately as is, or further processed to further alter the surface properties of hydrophilic substrate 30.

In one exemplary embodiment, functionalized substrate 30 is further processed to alter the surface properties of functionalized substrate 30. In this embodiment, functionalized substrate 30 is processed through a grafting process such as exemplary method 10 for a second time for even more times) in order to (i) graft additional grafting monomers onto interstitial and outer surfaces of functionalized substrate 30, (ii) graft additional monomers onto grafted species extending from interstitial and outer surfaces of functionalized substrate 30, or (iii) both (i) and (ii).

For example, in one exemplary embodiment, functionalized substrate 30 is prepared by coating a base substrate, preferably imbibing a porous base substrate, with a first solution comprising one or more grafting photoinitiator monomers (Formula XII) in a solvent, and then exposing the base substrate imbibed with the first solution to a controlled amount of ionizing radiation, preferably electron beam or gamma radiation, so as to graft the photoinitiator a) monomers to the surface(s) of the base substrate.

The resulting first functionalized substrate is optionally (but not preferably) rinsed to remove any unreacted grafting monomer, and may then be subsequently imbibed with a second solution comprising: (b) one or more of said ligand monomers, (c) optionally one or more monomers having at least one acryloyl group and at least one additional ethylenically unsaturated, free-radically polymerizable group; and (d) optionally one or more hydrophilic monomers; and then exposing the first functionalized substrate imbibed with the second solution to a controlled amount of electron beam radiation to form a second functionalized substrate having both photoinitiator groups, ligand groups and other optional groups. Free and ungrafted monomers are subsequently incorporated (indirectly grafted) to the base substrate during subsequent UV polymerization.

In another exemplary embodiment, functionalized substrate 30 is prepared by coating a base substrate, preferably imbibing a porous base substrate, with a first solution comprising one or more grafting hydrophilic monomers. This embodiment is particularly useful in rendering hydrophobic substrate such as PVDF substrate hydrophilic. The resulting first functionalized substrate is optionally (but not preferably) rinsed to remove any unreacted grafting monomer, and may then be subsequently imbibed with a second solution comprising: a) photoinitator monomers, (b) one or more of said ligand monomers, and (c) optionally one or more monomers having at least one acryloyl group and at least one additional ethylenically unsaturated, free-radically polymerizable group, and then exposing the first functionalized substrate imbibed with the second solution to a controlled amount of electron beam radiation to form a second functionalized substrate having both photoinitiator groups, ligand groups and other optional groups. Free and ungrafted monomers are subsequently incorporated (indirectly grafted) to the base substrate during subsequent UV polymerization.

Similarly, the second imbibing step may comprise only said photoinitiator monomers which are grafted by exposure to ionizing radiation, the functionalized article having both photoinitiator groups and hydrophilic groups are subjected to a third imbibing step with a third solution comprising (b) one or more of said ligand monomers, and (c) optionally one or more monomers having at least one acryloyl group and at least one additional ethylenically unsaturated, free-radically polymerizable group, which are subsequently indirectly grafted during subsequent UV polymerization.

The further modified functionalized substrate 30 can then proceed through an optional washing/rinsing step, such as exemplary washing/rinsing step 500 in exemplary method 10, and an optional drying step, such as exemplary drying step 600 in exemplary method 10. Subsequent to the two-step grafting process, the imbibed substrate can be further processed by the UV irradiation step.

In optional heating step (not shown), ligand functionalized substrate 30 is heated. Typically, during the optional heating step, ligand functionalized substrate 30 is subjected to an oven having an oven temperature of up to about 120° C. depending on a number of factors including, but not limited to, the reactants, the porous base substrate, the functional groups present on the grafted species, and the dwell time within oven 36. Typically, the oven temperature used in optional heating step is 30° C. of greater (desirably, 40° C. or greater, 50° C. or greater, or 60° C. or greater). The oven temperature typically ranges from about 60° C. to about 120° C. Typically, oven dwell time in optional heating step ranges from about 60 seconds to about 1 hour.

Any conventional oven may be used in the optional heating step of the present invention, such as optional heating step. Suitable ovens include, but are not limited to, the above-described ovens used in optional drying step 600 of exemplary method 10. Desirably, the oven used in optional heating step 800 of exemplary method 50 comprises a circulating air oven.

The ligand functionalized substrate 33 may be stored for future use in roll form, used immediately as is, or further processed in one or more additional process to steps (not shown). Suitable additional process steps may include, but are not limited to, a reaction step or a coating step wherein a coating composition is applied to further functionalized substrate 35, a lamination step wherein one or more additional layers are temporarily or permanently joined to further functionalized substrate 33, an assembling step wherein further functionalized substrate 33 is combined with one or more additional components to form a finished product (e.g., a filter assembly), a packaging step wherein further functionalized substrate 33 or a finished product comprising further ligand functionalized substrate 33 is packaged within a desired packaging material (e.g., a polyethylene film or bag), or any combination thereof.

The methods of making functionalized substrates of the present invention may also be described by one or more process parameters including, but not limited to, the process parameters provided below.

1. Batch Versus Continuous Process

It should be noted that the methods of making ligand functionalized substrates of the present invention may be performed using a continuous process, such as exemplary method 10 shown in FIG. 1, or alternatively, using a batch process wherein one or more of the above-described, process steps are performed separate from one another. Desirably, the methods of making functionalized substrates are performed using a continuous process, such as exemplary method 10 shown in FIG. 1.

2. Line Tension

When using a continuous process, such as exemplary method 10, one or more drive rolls (not shown) may be used to move porous base substrate 12 or functionalized substrate 30 through the continuous process. The one or more drive rolls provide sufficient tension on porous base substrate 12 and functionalized substrate 39 to move porous base substrate 12 and functionalized substrate 30 through a given apparatus. Care should be taken when determining the amount of tension to apply in order to prevent shrinkage and/or tearing of porous base substrate 12 or functionalized substrate 30 during processing. If a stronger carrier web (e.g., removable carrier layer 22) is used to convey base substrate 12 or functionalized substrate 30, then the tension load is easier to adjust without transmitting the tension load through the substrate itself.

In the exemplary continuous grafting process of the present invention, the one or more drive rolls typically operate in a range of 5 to 40 lbs (22 to 178 Newtons) of tension on a (12 inch) 30 cm wide web of porous base substrate 12 or functionalized substrate 30 in order to move porous base substrate 12 or functionalized substrate 30 through a given apparatus, resulting in a tension of 0.7 to 5.9 Newtons per lineal centimeter of porous base substrate 12 or functionalized substrate 30. In one desired embodiment, the one or more drive rolls operate in a range of 1.4 to 3.0 Newtons per lineal centimeter of porous base substrate 12 or functionalized substrate 30.

3. Line Speed

In the exemplary continuous grafting process of the present invention, the one or more drive rolls also provide a desired line speed through a given apparatus. Desirably, porous base substrate 12 and functionalized substrate 30 move through a given apparatus at a line speed of at least about 1.52 meter/minute (mpm) (5 fpm). In one desired embodiment, porous base substrate 12 and functionalized substrate 30 move through a given apparatus at a line speed ranging from about 3.05 mpm (10 fpm) to about 30.5 mpm (100 fpm).

The disclosed methods may be used to prepare a variety of ligand functionalized substrates. The ligand functionalized substrates have a polymerized coating derived from grafting followed by UV initiated polymerization from the grafted photoinitiator a), the ligand monomer b) and optionally one or more monomers having at least one acryloyl group and at least one additional ethylenically unsaturated, free-radically polymerizable group (c); and (d) optionally one or more hydrophilic monomers that may be directly or indirectly grafted.

In any of the above-described methods of making a functionalized substrate, any of the above-mentioned porous base substrates, grafting monomers, and reactants may be used to form a given functionalized substrate. The porous base substrate is often in the form of a porous membrane such as a microporous membrane, a nonwoven web, or porous fibers. In some embodiment, the porous base substrate comprises a microporous membrane formed by a thermally-induced phase separation (TIPS) method.

In one embodiment, the methods provide an article having a ligand functionalized coating on the surface thereof, the ligand functionalized coating comprising the UV polymerization reaction product of a grafted photoinitiator group and one or more ligand monomers, one or more ethylenically unsaturated polymerizable monomers and one or more hydrophilic monomers, which may be ungrafted acryloyl groups or other non-acryloyl ethylenically unsaturated polymerizable groups.

The method of making a ligand functionalized substrate alters the original nature of the porous base substrate, as the grafted and UV polymerized species include a ligand group.

The present invention enables the formation of ligand functionalized substrates having many of the advantages of a porous bases substrate (e.g. mechanical and thermal stability, porosity), but with enhanced affinity for biomolecules such as viruses, resulting from the monomers and steps used to form a given functionalized substrate. The present invention reduces or eliminates many of the known problems associated with porous bases substrates formed from hydrophilic polymers including, but not limited to, hygroexpansive issues; brittleness without humidification problems; mechanical strength weakness; and poor solvent, caustic and/or acidic resistance.

In one embodiment, the grafting monomer having a first grafting acrylate group and a second non-grafting ethylenically unsaturated polymerizable group may comprise hydrophilic groups, as illustrated in Formulas VII, VIII, X and/or XI (supra). For example, poly(alkylene oxide) compounds of Formulas VIII and/or XI can be used to impart a hydrophilic character to a hydrophobic base substrate, such as a PVDF substrate. These grafting monomers may have a hydrophilic poly(alkylene oxide) group.

Alternatively grafting monomers of Formulas IX or X may be used which do contain an ionic group. In these instances, hydrophilicity is imparted using a fourth monomer, which may contain a grafting acrylate group or a non-acrylate polymerizable group, and a hydrophilic group, such as a quaternary ammonium group. Such ionic groups may further impart enhanced selectivity to the functionalized substrate by repelling biological species having a like charge as the ionic group, at the appropriate pH.

The ligand-functionalized porous substrates are particularly suited as filter media, for the selective binding and removal of viruses from biological samples. As the ligand is grafted to the base substrate (either directly or indirectly), the ligand functionalized substrate is durable. The present disclosure then further provides a method for the removal of viruses from a virus-containing sample, such as a biological sample comprising contacting a sample with the ligand functionalized substrate as described herein.

The sample is contacted with the virus-trapping membrane for a time sufficient to a yield log-reduction value (LRV) of at least 1.0 for neutral viruses disposed in the solution when the solution comprises from 0 to about 50 mM salt, and more preferably still to a yield log-reduction value (LRV) of at least 1.0 for neutral viruses disposed in the solution when the solution comprises from 0 to about 150 mM salt. It is still more preferred that the solution is contacted with the virus-trapping membrane for a time sufficient to a yield log-reduction value (LRV) of at least 5.0 for neutral viruses disposed in the solution when the solution comprises from 0 to about 50 mM salt, and more preferably still to a yield log-reduction value (LRV) of at least 5.0 for neutral viruses disposed in the solution when the solution comprises from 0 to about 150 mM salt. The term neutral virus is used to denote any virus that has an isoelectric point (pI) around 7, or optionally, nominally between 6 and 8. The sample solution may a pH that is such that the virus is negatively charged.

This importance of viral clearance in the presence of salt, "salt tolerance", is that many process solutions used in biopharmaceutical manufacture have conductivities in the range of 15-30 mS/cm. Salt tolerance is measured in comparison to the conventional Q ligand (AETMA, 2-aminoethyltrimethylammonium chloride), which rapidly loses capacity for some viruses (e.g., $\phi$X174) at conductivities three- to six-fold less than the target range, e.g. dropping viral clearance from a six log-reduction value (LRV) to a one (1) LRV in going from 0 to 50 mM NaCl. Viruses such as $\phi$X174 have pIs close to 7, and are neutral or near-neutral.

In many embodiments the substrate may be functionalized so that other proteins are excluded or repelled from the ligand functionalized substrate, while viruses bind to the ligand functional group of Formulas V or VI. In addition, as previously described, the substrate may be directly or indirectly grafted with one or more ionic monomers. In particular, the porous substrate may comprise grafted ionic groups that are positively charged at the selected pH of the biological sample solution to cause electrostatic charge repulsion of proteins, such as monoclonal antibodies, many of which are charged positive at neutral pH.

Preventing protein binding, such as mAb binding, can be accomplished by increasing the pKa of the ligand, or grafting an additional positively charged functional group, so that the mAb and ligand are both charged positive daring loading. This causes electrostatic charge repulsion of the mAb from the ligand and substrate surface. The virus, in contrast, is either negatively charged or is neutral, and binds to the ligand. Most therapeutic mAbs tend to have pI's between 8 and 10. Thus, mAbs are positively charged at neutral pH, which prevents their binding to substrate surface. Viruses, on the other hand, can have a variety of pI's and many have negative pI's. Therefore the pH of the sample solution is below the isoelectric point of the protein of interest (such as a mAb) and above the isoelectric point of the virus.

The ligands and grafted functional groups herein are selected based on the above criteria and outcomes, i.e., it is salt tolerant and has a high pKa (e.g., >10) causing electrostatic charge repulsion of the mAb. The ligand is immobilized on a porous membrane and the virus-containing fluid flows through the membrane while the virus is trapped by the ligand.

In some embodiments the grafted article containing the bound virus is disposable. In such embodiments, the binding of the virus to the filter medium is preferably essentially irreversible because there is no need to recover the bound virus. Nonetheless, one can reverse the binding of viruses by increasing the ionic strength of an eluting solution. In contrast, in protein binding, the binding phenomenon must necessarily be reversible or the desired protein cannot be eluted from the column.

The substrate for viral capture may be any previously described, but is preferably a microporous membrane. The membrane pore size desired is from 0.1 to 10 μm, preferably 0.5 to 3 micrometers and most preferably 0.8 to 2 micrometers. A membrane with a high surface area for the internal pore structure is desired, which typically corresponds to fine pore sizes. However, if the pore size is too small, then the membrane tends to plug with fine particulates present in the sample solution.

If desired, efficiency of viral binding and capture may be improved by using a to plurality of stacked, ligand-functionalized porous membranes as a filter element. Thus the present disclosure provides a filter element comprising one or more layers of the porous, ligand functionalized substrate. The individual layers may be the same or different, and may have layers of different porosity, and degree of grafting by the aforementioned grafting monomers. The filter element may further comprise an upstream prefilter layer and downstream support layer. The individual filter elements may be planar or pleated as desired.

Examples of suitable prefilter and support layer materials include any suitable porous membranes of polypropylene, polyester, polyamide, resin-bonded or binder-free fibers (e.g., glass fibers), and other synthetics (woven and non-woven fleece structures); sintered materials such as polyolefins, metals and ceramics; yarns; special filter papers (e.g., mixtures of fibers, cellulose, polyolefins, and binders); polymer membranes; and others.

In another embodiment, there is provided a filter cartridge including the above-described filter element. In yet another embodiment there is provided a filter assembly comprising the filter elements and a filter housing. In a further embodiment, this invention relates to a method of viral capture comprising the steps of:

a) providing the filter ter element comprising one of more layers of the ligand functionalized base substrate of this disclosure, and b) allowing a moving biological solution containing a virus to impinge upon the upstream surface of the filter element for a time sufficient to effect binding of a virus.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Materials

"VAZPIA" refers to 2-propenoylaminoethanoic acid, 2-(4-(2-hydroxy-2-methylpropanoyl)phenoxy)ethyl ester prepared according to Example 1 of U.S. Pat. No. 5,506,279 (Babu et al.).

"PEG 400" Polyethyleneglycol, molecular weight 400, Aldrich Chemical Co.

"LUCIRIN TPO" is s 2,4,6-trimethylbenzoyl diphenyl phosphine oxide, available from BASF, Charlotte, N.C.

Electron beam irradiation was carried out using a Model CB-300 electron beam system, obtained from Energy Sciences, Inc., Wilmington, Mass. The film samples were placed between two sheets of poly(ethylene terephthalate) film for the irradiation.

The following procedure was adhered to unless otherwise specified. Samples of film were placed between two larger area size pieces of 4-mil thick PET and taped together at one end. This sandwich was then opened and the sample film was wetted with monomer solution and the sandwich reclosed. Trapped air bubbles were removed and excess liquid was squeezed out by gently applying a rubber roller over the surface of the sandwich. The sandwich was taped to a moving web of PET and conveyed through the electron beam processor at a speed of 20 fpm and at a voltage of 300 keV with sufficient beam current applied to the cathode to deliver the targeted dose. The beam was calibrated using thin film dosimeters, calibrated and traceable to a national standards laboratory (RISO, Denmark). In some cases, to lower the overall dose rate and increase residence time while under the beam, the dose was fractionated by multiple passes through the beam to simulate a longer exposure time more characteristic of electron beams with cathodes extended in the web direction (i.e. BroadBeam, etc).

Testing of Membranes
Ligand Determination:

The amount of ligand grafted was determined by % N present in the membrane. Samples were analyzed for weight percent nitrogen by combustion using a LECO 932 CHNS elemental analyzer. Samples were prepared by cutting small sections to from the center of each membrane with clean scissors. The sample sizes ranged from about 0.7-2.0 mg and were run in triplicate.

Water Flux Test:

Water flux was determined by placing a disk of the test film having a diameter of approximately 47 millimeters (1.85 inches) in a Model 4238 Pall Gelman magnetic filter holder (available from Pall Corp., East Hills, N.Y.). The filter holder was then placed on a filter flask that was attached to a vacuum pump. A vacuum gauge was used to monitor the vacuum. Approximately 150 milliliters of water was placed in the filter holder and then vacuum was applied. After approximately 50 milliliters of water passed through the film (the vacuum gauge at this time indicated approximately 0.83 millimeters of mercury (approximately 10 psi), timing was commenced using a stopwatch. When all of the remaining water bad passed through the film, timing was stopped. The water flux was the time, measured in seconds, which elapsed for 100 milliliters of water to pass through the membrane under a vacuum of 0.83 millimeters of mercury.

Binding of Bovine Serum Albumin:

The membranes were analyzed for binding of proteins by passing solutions of the test analytes through a 6-layer stack of the membranes punched out into 25-mm diameter discs placed in a 25 mm diameter holder attached to an AKTA chromatography system (GE Healthcare, NY). Bovine scrum albumin (BSA) from Sigma was prepared as a solution of concentration 1 mg/ml in 25 mM TRIS-HCl buffer at pH 8. The BSA solution was flowed through the membrane stack at a flow rate of 1 ml/mm and the UV absorbance of the effluent was monitored at a wavelength of 280 nm. The dynamic binding capacity of the membrane was evaluated using standard chromatography techniques.

Determination of Viral Capture:

Viral capture was measured using a standard protocol developed at the Food and Drug Administration as described in the PDA Technical Report 41 (TR41), Virus Filtration. The test virus was a bacteriophage ϕX-174. A standard stock solution containing $10^9$ pfu/ml (plaque forming units) in a 10 mM TRIS-HCl buffer at pH 7.5, with a NaCl concentration of 150 mM was prepared. This stock was flowed through the membrane stack as previously described. The effluent was collected as 1 ml fractions using a fraction collector. Fractions corresponding to a total throughput of 10 ml, 20 ml, 30 ml, 40 ml and 50 ml through the membranes were taken aside and these were subjected to several decadal dilutions. The virus stock solution was also subjected to a similar dilution series. The diluted fractions were then incubated with *E. coli* solutions and plated onto agar plates along with growth medium comprised of tryptic soy broth. The plates were incubated overnight and the numbers of dead plaques was counted. The LRV (or log reduction in viral load) was estimated from knowledge of the corresponding dilution factor as well as the initial concentration of the phage.

Hydrophilic PVDF Membranes:

Microporous poly(vinylidine fluoride) (PVDF), about 5 mils thick (~127 micrometers), 72% porosity, Gurley (air flow) about 4.5 sec/50 cc, 1.4 um average pore size and 1.9 um bubble point pore size (largest effective pore size) and a water flux time of about 10 sec (100 ml, 47 mm holder, 23 in Hg vacuum) was prepared using the general procedure described in U.S. Pat. No. 7,318,692 (Smith et al.). The PVDF microporous film was rendered hydrophilic by imbibing with a 10 wt. % solution of polyethylene glycol diacrylate (available as Sartomer 344™, SARTOMER Company, Inc., Exton, Pa.) in methanol. The wetted membrane was then placed into a sandwich with 2 layers of poly(ethylene terephthalate) film and subjected to electron beam radiation at 2 Mrad at a voltage of 300 keV. The membrane was then released from the sandwich and then washed 3 times with water and dried.

Nylon Membranes:

Nylon membranes were prepared using the general procedure described in U.S. Pat. No. 6,413,070 (Meyering, et al.) The membrane is prepared from an injection molding grade of Nylon 66, where the majority of polymer chains contain amine terminated end-groups. The membrane is a single reinforced layer nylon three zone membrane, where all three zones are equivalent pore size and composition. The membrane is a single reinforced layer nylon three zone membrane, where all three zones are equivalent pore size and composition. The membrane has a nominal Coulter Mean Flow Pore of 1.5 micron, a Forward Flow Bubble Point in 60:40 isopropanol/water of approximately 6 psi (~41 kPa), and a nominal thickness of 6 mils (~152 micrometers). The membrane is supported on a reinforcing scrim of calendered, spunbonded polyester of approximately 1 oz/square yard (~33 g/m²) the, and is isotropic throughout.

Ligand and Grafting Examples

Comparative Example 1

Coupling of Agmatine on Activated PVDF Membranes

PVDF membranes were made functionalized with allyl groups by imbibing hydrophilized PVDF membranes with 20% solutions of $CH_2$=$CHCONHC(CH_3)_2$ $CONHCH_2CH$=$CH_2$. This monomer is a vinyl dimethylazlactone (VDM) adduct with allylamine. The allyl groups were then converted to bromohydrin groups and the resultant membrane was treated with agmatine sulfate to render the surfaces with agmatine groups. The LRV for these membranes were found to be 6. This allowed for designing monomers containing the guanidinium group to provide a facile way of imparting these groups on a membrane.

Example 2

Preparation of Acrylamidoagmatine

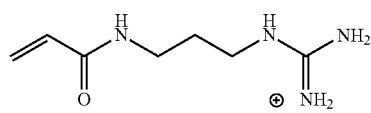

The procedure for synthesizing this monomer was adapted from U.S. Pat. No. 7,294,743.

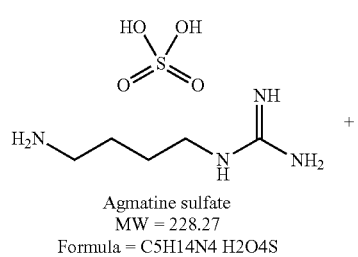

Agmatine sulfate
MW = 228.27
Formula = C5H14N4 H2O4S

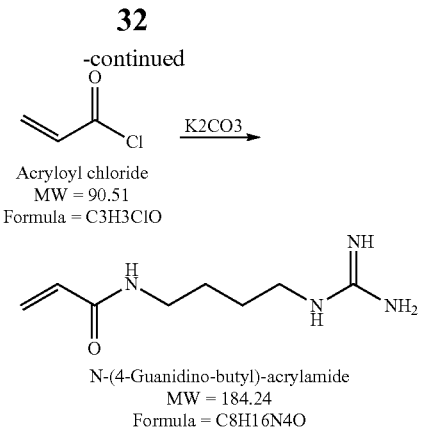

Acryloyl chloride
MW = 90.51
Formula = C3H3ClO

N-(4-Guanidino-butyl)-acrylamide
MW = 184.24
Formula = C8H16N4O

Procedure:

Agmatine sulphate (9.12 g, 40 mmol) was dissolved in distilled water (20 mL) in a round-bottom flask (100 mL equipped with as magnetic stirrer. $K_2CO_3$ (16.56 g, 100 mmol), dissolved in water (20 mL), was added to the round-bottom flask. The reaction mixture was cooled down on an ice bath and the mixture was stirred for 10 minutes at 5° C. Acryloyl chloride (7.24 g, 6.50 mL, 80 mmol), dissolved in acetone (20 mL) was added drop wise to the flask using a Pasteur-pipette. The reaction was allowed to proceed at 5° C. for 1 h. The stirring was then stopped. The aqueous phase was then fixed to pH 2.3 with concentrated sulfuric acid and then filtered on a glass filter. The aqueous phase was then extracted with methyl isobutyl ketone (MIBK, 2×100 mL) to remove excess acrylic acid formed during the reaction. The pH of the aqueous phase was then fixed to pH 7 by addition of $K_2CO_3$ and the final clear solution was utilized for grafting.

Grafting of Acrylamidoagmatine:

The acrylamidoagmatine was grafted onto hydrophilic PVDF membranes by electron beam radiation. Two different approaches were used:

2a: Direct: The hydrophilic PVDF membrane was imbibed with the acrylamidoagmatine solution using a plastic pipette and a squeezing roller for uniformity. The wetted membrane was then placed into a sandwich with 2 layers of PET and subjected to electron beam radiation at 4 Mrad. Ile membrane was then released from the sandwich and then washed 3 times with water and dried.

2b: Indirect: The hydrophilic PVDF membrane was sandwiched between 2 layers of PET liner and exposed to electron beam at a dose of 4 mrad to get a substrate rich in free radicals. This sandwich was then transferred to an inert atmosphere in a glove box. The acrylamidoagmatine solution was imbibed into the membrane and the wetted membrane was transferred to a Ziploc bag and stored overnight. The membrane was then washed three times in a water bath and then dried in ambient.

In the direct approach, the monomer is exposed to the radiation. There is a possibility that homopolymer formation could occur in solution, without grafting to the membrane. In the indirect approach, the monomer is not exposed to the radiation and chain growth from the surface of the membranes is a more facile process.

A sample membrane derivatized with acrylamidoagmatine by the direct method gave a % N of 0.247, corresponding to a ligand loading 44 µmol/g membrane.

Example 3

Grafting or Acrylamidoagmatine by Gamma Radiation

Four acrylagmatine/water solutions were made, 1%, 2%, 3%, and 4% respectively from a 27% acrylagmatine concentrate. These were imbibed onto hydrophilic PVDF and nylon film samples. The eight film samples were sandwiched between PET liners, clamped into a flame, and placed into an airtight aluminum tote. The tote was purged of air and filled with $N_2$. These films were irradiated with gamma radiation to 12 kGy, (which corresponded to a time duration of 2 hours). The weight gain for each piece is recorded in Table 1. (The starting weights of the films are about 2.8 grams each for a nominal 6"×8" sized sheet.)

TABLE 1

Weight Gain after Gamma Irradiation

| Film Sample | Weight gain (mg) | Flux 100 ml, 21 in Hg 47 mm (sec) |
|---|---|---|
| hydrophilic PVDF 1% Agmatine Solution | 0.4 | 26.3 |
| hydrophilic PVDF 2% Agmatine Solution | 3.0 | 36.1 |
| hydrophilic PVDF 3% Agmatine Solution | 6.5 | 53.6 |
| hydrophilic PVDF 4% Agmatine Solution | 12.6 | 78.0 |
| nylon 1% Agmatine Solution | 27.1 | 13.2 |
| nylon 2% Agmatine Solution | 20.0 | 16.5 |
| nylon 3% Agmatine Solution | 24.6 | 24.0 |
| nylon 4% Agmatine Solution | 42.0 | 36.0 |

Example 4

Preparation of Membranes Containing Agmatine Analogs

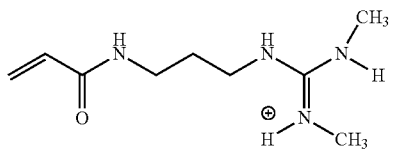

The N,N'-dimethyl guanidinium derivative of agmatine having essentially the same pKa values as agmatine was synthesized. The ligand provided 5 log reduction with no salt present comparable to the commercially available Mustang Q™ membrane (a porous polyethersulfone membrane functionalized so as to have quaternary ammonium groups on the surface available from Pall Life Sciences, Arm Arbor, Mich.) but failed completely at 50 mM NaCl. The acrylamide derivative above was synthesized and suggests that a hydrogen bonding affinity interaction (possibly with peripheral amide groups on the virus) may be required and is available only with unsubstituted guanidinium groups.

Example 5

Preparation of Acrylamidoarginine

A corresponding acrylamide derived from aminoacid arginine was prepared.

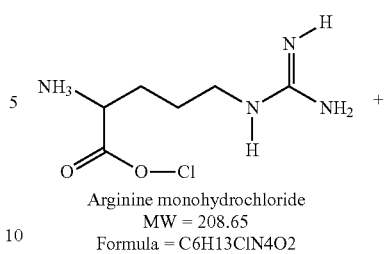

Arginine monohydrochloride
MW = 208.65
Formula = C6H13ClN4O2

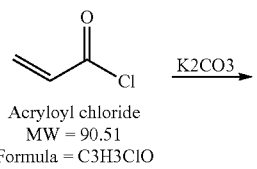

Acryloyl chloride
MW = 90.51
Formula = C3H3ClO

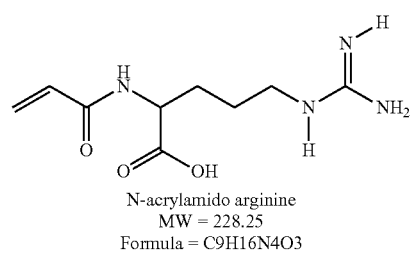

N-acrylamido arginine
MW = 228.25
Formula = C9H16N4O3

Procedure:

Arginine monohydrochloride (4.17 g, 20 mmol) was dissolved in distilled water (10 mL) in a round-bottom flask (100 ml.) equipped with a magnetic stirrer. $K_2CO_3$ (8.28 g, 50 mmol), dissolved in water (10 mL), was added to the round-bottom flask. The reaction mixture was cooled down on an ice bath and the mixture was stirred for 10 minutes at 5° C. Acryloyl chloride (3.62 g, 3.25 mL, 40 mmol), dissolved in acetone (10 mL) was added drop wise to the flask using a Pasteur-pipette. The reaction was allowed to proceed at 5° C. for 1 h. The stirring was then stopped. The aqueous phase was then fixed to pH 2.3 with concentrated sulfuric acid and then filtered on a glass filter. The aqueous phase was then extracted with methyl isobutyl ketone (MIBK, 2×100 mL) to remove excess acrylic acid formed during the reaction. The pH of the aqueous phase was then fixed to pH 7 by addition of $K_2CO_3$, cooled with liquid nitrogen and the water removed by freeze-drying. The final white fluffy solid was then dissolved in MeOH, filtered, and the MeOH was removed by rotoevaporation at 40° C. The film was taken up in $H_2O$ and freeze dried to afford a white fluffy solid When the positive charge of the guanidinium group was neutralized by the negative charge of the carboxylate (at pH 7.4), no bacteriophage binding (even with no additional salt added) was observed clearly indicating that a positive charge on the overall ligand assembly is desired. In this case two positive charges, one for the α-amine group and the other with the guanidine group, will be present along with an unsubstituted guanidinium unit.

Example 6

Preparation of IEM-Agmatine Adduct

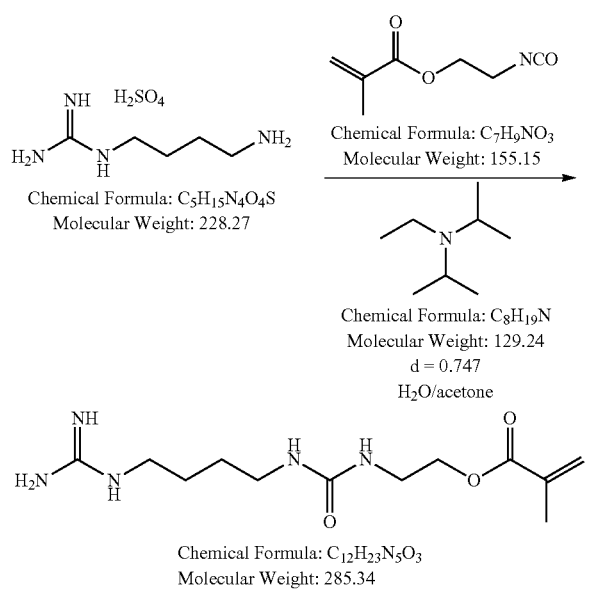

42 g agmatine sulfate (AGM; 184 mmol) was stirred in a mixture of distilled water (300 ml) and acetone (300 ml). Diisopropylethylamine (DIEA: 32 ml, 184 mmol) was added to the solution, followed by drop-wise addition of isocyanatoethylmethacrylate IEM: 32 ml, 206 mmol) over 15 minutes. The solution became clear as the addition of IEM. The reaction was stirred for 4 hours. NMR of the crude reaction solution indicated clean conversion. The volatile components of the reaction, acetone and excess DIEA, was removed under vacuum. The remaining aqueous solution was frozen, and freeze-dried under high vacuum. After 48 hours of lyophilization, 94 g, of white powder was obtained. The total mass collected, 94 grams, contained the desired IEM-AGM, but also other side-products: sulfuric acid and DIEA. The w/w percentage of the active ingredient, the methacrylate monomer, is 53.5% (w/w) of the total mass.

Grafting of the IEM-Agmatine Adduct

The IEM-agmatine adduct was grafted onto hydrophilized PVDF and nylon membranes by procedures similar to that used in Example 2 for acrylamidoagmatine. In addition, a two-stage process was employed as described hereunder.

6a: Direct: The hydrophilized PVDF membrane was imbibed with a 16% IEM-agmatine solution in methanol using a plastic pipette and a squeezing roller for uniformity. The wetted membrane was then placed into a sandwich with 2 layers of PET and subjected to electron beam radiation at 4 mrad. The membrane was then released from the sandwich and then washed 3 times with water and dried. The procedure was repeated on a nylon substrate.

6b: Indirect: The hydrophilized PVDF membrane was sandwiched between 2 layers of PET liner and exposed to electron beam at a dose of 4 mrad to get a substrate rich in free radicals. This sandwich was then transferred to an inert atmosphere in a glove box. The 10% IEM-agmatine solution in methanol was imbibed into the membrane and the wetted membrane was transferred to a Ziploc bag and stored overnight. The membrane was then washed three times in a water bath and then dried in ambient.

6c: Two stage process: The first functionalizing E-beam irradiation process was done with a dose of 4 Mrad set at a voltage of 300 keV. The coating solution contained 5.0% 2% 3-(Acryloxy)-2-hydroxypropylmethacrylate with 1.0% VAZPIA in Methanol. The coating solution was imbibed into the hydrophilic TIPS PVDF microporous membrane. The sample was conveyed through the beam on a web carrier and was sandwiched 'wet' between layers of 4 mil PET in order to delay the diffusion of oxygen back into the membrane when it exited the beam chamber. After three minutes the sandwich was opened and the membrane was allowed to dry. (Any unreacted monomers from this step were allowed to remain.)

In the second functionalizing step, the molecule used was IEM-agmatine. The coating solution contained 10.0% IEM-AGM in methanol. The coating solution was imbibed into the coated TIPS PVDF microporous membrane and the sandwich was closed with any trapped air removed with as roller. The samples were then UV irradiated using Quant 48™ Quantum Technologies system using UVA lamps and run under the UV processor at a speed of about one foot per minute (4 feet exposure length, single side at 31 mW/cm$^2$). The sample sandwich was turned over and run again at the same speed. The grafted porous membrane was removed from the sandwich and was washed clean by soaking it in a tray of water and exchanging it with clean water three times. The functionalized membrane was allowed to air dry. The procedure was repeated on a nylon substrate.

Example 7

Preparation of Aminoguanidine-Vinyldimethylazlactone Adduct

A 250 ml, round bottomed flask was charged with aminoguanidine hydrochloride (1.1 g, TCI, Portland, Oreg.), isopropanol (100 mL), and vinyldimethylazlactone (1.39 g). With magnetic stirring, anhydrous sodium carbonate (3.2 g) was added, and the mixture was stirred overnight (ca. 16 hours). The reaction mixture was filtered and the solvent was removed on a rotary evaporator to give 2.25 g colorless solid. $^1$H-NMR (d$^4$-methanol) indicated the absence of starting materials, and clean conversion to a mixture of acrylamidoacylated products.

Example 8

Preparation of Vinyldimethylazlactone-Guanidine Adduct

A 250 mL round bottomed flask was charged with guanidine hydrochloride (1.08 g, EMD Chemicals), isopropanol (50 mL), and vinyldimethylazlactone (1.57 g). With magnetic stirring, anhydrous sodium carbonate (2.4 g) was added, and the mixture was stirred overnight (ca. 16 hours). The reaction mixture was filtered and the solvent was removed on a rotary evaporator to give 2.53 g colorless, foamy solid. $^1$H-NMR (d$^4$-methanol) indicated the absence of starting materials, and was consistent with the expected acrylamidoacylated guanidine product.

TABLE 2

| Ex. | Ligand/substrate | Graft method | % ligand umol/g | Water flux (s) | BSA DBC (mg/ml) | LRV (150 mM NaCl) |
|---|---|---|---|---|---|---|
| C1 | VDM_Allylamine adduct/Agmatine on PVDF | Covalent coupling | — | — | — | 6 |
| 2a | Acrylamidoagmatine/PVDF | Direct ebeam | 45 | 18 | 14 | 2 |
| 2b | Acrylamidoagmatine/PVDF | Indirect | 115 | | 0.6 | 3 |
| 3 | 4% Acrylamidoagmatine/nylon | Gamma | — | 36 | 12 | 7 |
| 3 | 4% Acrylamidoagmatine/PVDF | Gamma | 31 | 78 | 23 | 5 |
| 4a | IEM-Agmatine/PVDF | Direct | 185 | | 37 | 8 |
| 4a | IEM-Agmatine/Nylon | Direct | — | | 55 | 6 |
| 4b | IEM-Agmatine/PVDF | Indirect | 317 | 14 | 59 | 2 |
| 4c | IEM-Agmatine/PVDF | 2-stage | 476 | 14 | 88 | 7 |
| 4c | IEM-Agmatine/Nylon | 2-stage | — | 23 | 50 | 8 |

What is claimed is:

1. A method of making a ligand functionalized substrate, the method comprises the steps of:
   1) providing a base substrate;
   2) coating the substrate with a solution comprising (a) at least one grafting monomer having an acryloyl group and a photoinitiator group; (b) one or more ligand monomers of the formula:

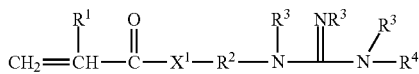

wherein
   $R^1$ is H or $C_1$-$C_4$ alkyl,
   $R^2$ is a divalent alkylene optionally containing an ester, amide, urethane or urea linking group;
   each $R^3$ is independently H or $C_1$-$C_4$ alkyl,
   $R^4$ is H, $C_1$-$C_4$ alkyl or —N$(R^3)_2$; and
   $X^1$ is —O— or —NR$^3$—, (c) optionally one or more monomers having at least one acryloyl group and at least one additional ethylenically unsaturated, free-radically polymerizable group; and (d) optionally one or more hydrophilic monomers;
   3) exposing the coated base substrate to ionizing radiation to form a first functionalized substrate comprising grafted photoinitiator groups attached to the surface of the base substrate and unreacted (b), (c) and (d) monomers having ethylenically unsaturated, free-radically polymerizable groups, and
   4) exposing the base substrate comprising grafted photoinitiator groups to UV radiation to polymerize the remaining ethylenically unsaturated, free-radically polymerizable groups of the (b), (c) and (d) monomers.

2. The method of claim 1 wherein said substrate is a porous substrate having interstitial and outer surfaces.

3. The method of claim 2 wherein the step of coating comprises imbibing the porous base substrate with the solution.

4. The method of claim 1 wherein said ionizing radiation is gamma or electron beam radiation.

5. The method of claim 1 wherein said monomers (c) having least one acryloyl group and at least one additional ethylenically unsaturated, free-radically polymerizable group comprises a first acryloyl group for grafting to said porous base substrate and a second methacryloyl group for subsequent UV polymerization.

6. The method of claim 1 wherein said monomer c) is of the formula:

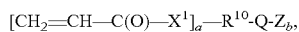

where Z is an acryloyl or non-acryloyl, ethylenically unsaturated polymerizable group,
   $X^1$ is —O— or —NR$^3$, where $R^3$ is H or $C_1$-$C_4$ alkyl,
   Q is a divalent linking group selected from a covalent bond, —O—, —NR$^1$—, —CO$_2$— and —CONR$^1$—, where $R^1$ is H or $C_1$-$C_4$ alkyl; and
   $R^{10}$ is an alkylene group, and optionally containing one or more ether oxygen atoms and/or one or more hydroxyl groups;
   and a and b are each at least one.

7. The method of claim 1, wherein the base substrate is microporous.

8. The method of claim 1, wherein the base substrate is selected from a porous membrane, porous non-woven web, or porous fiber.

9. The method of claim 1, wherein the monomer c) comprises a poly(alkylene oxide) compound having at least one acryloyl group and at least one additional ethylenically unsaturated, free-radically polymerizable group.

10. The method of claim 9, wherein the monomer c) is of the formula:

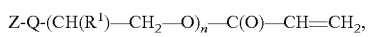

wherein Z is an acryloyl or non-acryloyl, polymerizable ethylenically unsaturated group, $R^1$ is a H or a $C_1$ to $C_4$ alkyl group, and n is from 2 to 100, and Q is a divalent linking group selected from a covalent bond, —O—, —NR$^1$—, —CO$_2$— and —CONR$^1$—, where $R^1$ is H or $C_1$-$C_4$ alkyl.

11. The method of claim 1, wherein said solution comprises one or more additional monomers having a free-radically polymerizable group and a hydrophilic group.

12. The method of claim 1 wherein said hydrophilic monomers are of the formula:

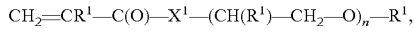

wherein each $R^1$ is independently H or $C_1$-$C_4$ alkyl, $X^1$ is —O— or —NR$^3$—, where $R^3$ is H or $C_1$-$C_4$ alkyl.

13. The method of claim 7, wherein the microporous base substrate is formed by a thermally-induced phase separation (TIPS) method.

14. The method of claim 7, wherein the microporous base substrate comprises poly(vinylidine fluoride) microporous base substrate.

15. The method of claim 1, wherein the ionizing radiation is electron beam radiation at a dosage of less than 80 kGy.

16. The method of claim 1 wherein said ligand monomer is the formula:

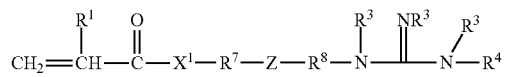

where
$R^1$ is H or $C_1$-$C_4$ alkyl,
each $R^3$ is independently H or $C_1$-$C_4$ alkyl,
$R^4$ is H, $C_1$-$C_4$ alkyl or —$N(R^3)_2$,
$X^1$ is —O— or —$NR^3$—, where $R^3$ is H or $C_1$-$C_4$ alkyl,
$R^7$ and $R^8$ are each independently is $C_1$ to $C_{10}$ alkylene; and
Z is an ester, amide, urea, or urethane group.

* * * * *

UNITED STATES PATENT AND TRADEMARK OFFICE
CERTIFICATE OF CORRECTION

Page 1 of 4

PATENT NO. : 8,652,582 B2
APPLICATION NO. : 12/937458
DATED : February 18, 2014
INVENTOR(S) : Catherine A. Bothof et al.

It is certified that error appears in the above-identified patent and that said Letters Patent is hereby corrected as shown below:

In the Specification

Column 1,
Line 44, delete "resultant" and insert -- resultant, --, therefor.
Line 53, delete "as" and insert -- a --, therefor.

Column 2,
Line 60, delete "ate" and insert -- the --, therefor.

Column 3,
Line 66, delete "remaining," and insert -- remaining --, therefor.

Column 4,
Line 1, delete "wafting" and insert -- grafting --, therefor.
Line 39, delete "as" and insert -- a --, therefor.
Line 48, before "polyamides," delete "is".

Column 5,
Line 18, delete "molded;" and insert -- molded, --, therefor.
Line 28, delete "rising" and insert -- using --, therefor.
Line 31, delete "crosslinking," and insert -- crosslinking --, therefor.
Line 34, delete "site" and insert -- size --, therefor.

Column 6,
Line 18, delete "as" and insert -- a --, therefor.
Line 22, delete "firmed" and insert -- formed --, therefor.
Line 49, delete "uric" and insert -- one --, therefor.

Signed and Sealed this
Twenty-second Day of July, 2014

Michelle K. Lee
*Deputy Director of the United States Patent and Trademark Office*

CERTIFICATE OF CORRECTION (continued)
U.S. Pat. No. 8,652,582 B2

Column 8,
Line 29, delete "grating" and insert -- grafting --, therefor.
Line 50, delete "—(CH$_2$)$_d$O—" and insert -- —(CH$_2$)$_d$ O— --, therefor.

Column 9,
Line 14, before "G" insert -- is --.

Column 10,
Line 36, delete "2.0" and insert -- 20 --, therefor.
Line 67, delete "C to C$_1$" and insert -- C$_1$ --, therefor.

Column 13,
Line 17, delete "and or" and insert -- and/or --, therefor.
Line 27, delete "-(M$^b$)$_x$," and insert -- -(M$^b$)$_x$ --, therefor.
Line 35, after "provide" insert -- a --.
Line 67, delete "containing," and insert -- containing --, therefor.

Column 14,
Line 25, delete "—NR—$^1$—," and insert -- —NR$^1$—, --, therefor.
Line 47, delete "ally" and insert -- allyl --, therefor.
Line 64, delete "preferably," and insert -- preferably --, therefor.

Column 15,
Line 66, delete "meth)" and insert -- (meth) --, therefor.

Column 16,
Line 27, delete "3-meth)" and insert -- 3-(meth) --, therefor.
Lines 54-55, delete "substituted," and insert -- substituted --, therefor.

Column 17,
Line 28, delete "N-(2" and insert -- N-(3 --, therefor.

Column 18,
Line 24, delete "XI" and insert -- XI, --, therefor.
Line 59, delete "baving" and insert -- having --, therefor.

Column 19,
Line 38, delete "PB" and insert -- EB --, therefor.
Line 44, delete "entitled"Practice" and insert -- entitled "Practice --, therefor.
Line 67, delete "amide" and insert -- guide --, therefor.

Column 20,
Line 29, delete "not" and insert -- (not --, therefor.

Column 21,
Line 18, delete "at" and insert -- a --, therefor.

Column 22,
Line 9, before "passes" delete "so".
Line 10, delete "e.g.," and insert -- (e.g., --, therefor.
Line 27, delete "front" and insert -- from --, therefor.
Line 35, delete "farce" and insert -- force --, therefor.
Line 38, delete "in" and insert -- improve --, therefor.
Line 47, delete "and or" and insert -- and/or --, therefor.
Line 53, after "multilayer" delete "or".

Column 24,
Line 18, delete "for" and insert -- (or --, therefor.

Column 25,
Line 40, before "steps" delete "to".
Line 63, delete "above-described," and insert -- above-described --, therefor.

Column 26,
Line 7, delete "39" and insert -- 30 --, therefor.

Column 28,
Line 17, delete "daring" and insert -- during --, therefor.
Line 54, before "plurality" delete "to".

Column 29,
Lines 1 and 2, delete "metals" and insert -- metals, --, therefor.
Line 11, delete "filter ter" and insert -- filter --, therefor.

Column 30,
Line 2, before "from" delete "to".
Line 17, delete "bad" and insert -- had --, therefor.
Line 27, delete "scrum" and insert -- serum --, therefor.
Line 31, delete "ml/mm" and insert -- ml/min --, therefor.
Line 63, delete "7,318,692" and insert -- 7,338,692 --, therefor.

Column 31,
Line 8, delete "(Meyering," and insert -- (Meyering --, therefor.

Column 32,
Line 20, delete "as" and insert -- a --, therefor.
Line 41, delete "Ile" and insert -- The --, therefor.
Line 59, after "loading" insert -- of --.

CERTIFICATE OF CORRECTION (continued)
U.S. Pat. No. 8,652,582 B2

Column 33,
Line 3, delete "flame," and insert -- frame, --, therefor.
Line 53, delete "Arm" and insert -- Ann --, therefor.

Column 34,
Line 42-43, delete "(100 ml.)" and insert -- (100 mL) --, therefor.

Column 35,
Line 46, delete "94 g," and insert -- 94 g --, therefor.

Column 36,
Line 23, delete "as" and insert -- a --, therefor.
Line 41, delete "250 ml," and insert -- 250 mL --, therefor.
Line 62, delete "(ca." and insert -- (ca, --, therefor.

UNITED STATES PATENT AND TRADEMARK OFFICE
CERTIFICATE OF CORRECTION

| | | |
|---|---|---|
| PATENT NO. | : 8,652,582 B2 | Page 1 of 1 |
| APPLICATION NO. | : 12/937458 | |
| DATED | : February 18, 2014 | |
| INVENTOR(S) | : Bothof et al. | |

It is certified that error appears in the above-identified patent and that said Letters Patent is hereby corrected as shown below:

Title Page,
First column, item (75), under inventors, please delete "Jerald K. Rasmussen, Woodville, MN" and insert -- Jerald K. Rasmussen, Woodville, WI --.

Signed and Sealed this
Tenth Day of November, 2015

Michelle K. Lee
*Director of the United States Patent and Trademark Office*